(12) United States Patent
Zhu et al.

(10) Patent No.: US 12,102,658 B2
(45) Date of Patent: Oct. 1, 2024

(54) TRIPEPTIDE PROPYLENE OXIDE DERIVATIVE AND PREPARATION METHOD AND APPLICATION THEREOF

(71) Applicant: SHENZHEN JIKANG PHARMACEUTICAL TECHNOLOGY CO., LTD, Shenzhen (CN)

(72) Inventors: Yongqiang Zhu, Nanjing (CN); Meng Lei, Nanjing (CN); Haoyang Zhang, Nanjing (CN)

(73) Assignee: SHENZHEN JIKANG PHARMACEUTICAL TECHNOLOGY CO., LTD, Shenzhen (CN)

( * ) Notice: Subject to any disclaimer, the term of this patent is extended or adjusted under 35 U.S.C. 154(b) by 904 days.

(21) Appl. No.: 16/977,329

(22) PCT Filed: Jan. 3, 2020

(86) PCT No.: PCT/CN2020/070197
§ 371 (c)(1),
(2) Date: Sep. 1, 2020

(87) PCT Pub. No.: WO2020/244224
PCT Pub. Date: Dec. 10, 2020

(65) Prior Publication Data
US 2023/0136796 A1    May 4, 2023

(30) Foreign Application Priority Data
Jun. 5, 2019 (CN) .......................... 201910485689.4

(51) Int. Cl.
*A61K 38/06* (2006.01)
*A61P 35/00* (2006.01)
*C07K 5/08* (2006.01)

(52) U.S. Cl.
CPC .............. *A61K 38/06* (2013.01); *A61P 35/00* (2018.01); *C07K 5/08* (2013.01)

(58) Field of Classification Search
None
See application file for complete search history.

(56) References Cited

FOREIGN PATENT DOCUMENTS

WO    WO-2008140782 A2 * 11/2008    ............. C07K 5/081

OTHER PUBLICATIONS

Costello et al. (Pancreat Disord Ther; Suppl 4; doi:10.4172/2165-7092.S4-002) (Year: 2013).*
Wang et al. (Proc Natl Acad Sci USA. Mar. 24, 2020;117(12):6640-6650) (Year: 2020).*

* cited by examiner

*Primary Examiner* — Sergio Coffa
(74) *Attorney, Agent, or Firm* — CBM PATENT CONSULTING, LLC

(57) ABSTRACT

The present invention discloses a tripeptide propylene oxide derivative or a pharmaceutically acceptable salt thereof, and a preparation method and application thereof. The structure of the tripeptide propylene oxide derivative is shown in formula I. Compared with the prior art, the present invention provides tripeptide epoxy ketone compounds with a novel structure and a function of inhibiting proteasome. As 20S proteasome inhibitors, the tripeptide epoxy ketone compounds can block tumor cell proliferation and induce tumor cell apoptosis, so the tripeptide epoxy ketone compounds can be used for the treatment and prevention of a plurality of human and animal diseases such as malignant tumors, and the effect is significantly better.

3 Claims, 2 Drawing Sheets

TRIPEPTIDE PROPYLENE OXIDE DERIVATIVE AND PREPARATION METHOD AND APPLICATION THEREOF

TECHNICAL FIELD

The present invention belongs to the field of pharmaceutical chemistry, and specifically relates to a new type of tripeptide propylene oxide derivative and a preparation method and pharmaceutical application thereof.

BACKGROUND ART

At present, malignant tumors are still one of the main diseases threatening people's lives. Although the treatment of cancer has made great progress, cancer cannot be treated fundamentally. Although the anti-cancer drugs currently on the market have certain curative effects, most of them are cytotoxic drugs with serious toxic and side effect. Therefore, how to study targeted new anti-cancer drugs from effective tumor targets has become a top priority for medical and pharmaceutical workers.

Ubiquitin-proteasome pathway (UPP) can regulate the level of proteins involved in cell cycle control. The pathway has an important relationship with the onset of cancer, cardiovascular and cerebrovascular diseases, and degenerative diseases of the nervous system. Using some effective inhibitors to inhibit the pathway from over-degrading important proteins can provide new ideas for the treatment of the above diseases.

SUMMARY OF THE INVENTION

Objective of the Present Invention

The objective of the present invention is to provide tripeptide epoxy ketone compounds with a novel structure and a function of inhibiting proteasome. As 20S proteasome inhibitors, the tripeptide epoxy ketone compounds can block tumor cell proliferation and induce tumor cell apoptosis, so the tripeptide epoxy ketone compounds can be used for the treatment and prevention of a plurality of human and animal diseases such as malignant tumors.

Another objective of the present invention is to provide a preparation method of the above compound.

Yet another objective of the present invention is to provide application of the above compound in preparation of anti-tumor drugs.

Technical Solution

In order to achieve the above objectives of the present invention, the present invention adopts the following technical solutions:

A tripeptide propylene oxide derivative or a pharmaceutically acceptable salt thereof is provided. The structure of the tripeptide propylene oxide derivative is shown in formula I:

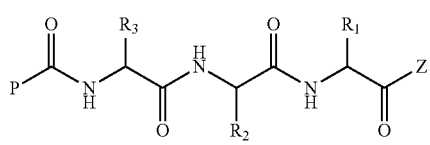

(I)

where:
$R_1$ is selected from hydrogen, deuterium, $C_{1-10}$ alkyl, $C_{3-6}$ cycloalkyl, heterocycloalkyl, heterocyclyl, aryl or benzyl, and the $C_{1-10}$ alkyl, $C_{3-6}$ cycloalkyl, heterocycloalkyl, heterocyclyl, aryl or benzyl is optionally substituted or unsubstituted by $C_{1-4}$ alkyl, $C_{1-4}$ alkoxyl, $C_{1-4}$ alkylthio, cyano, nitro, hydroxyl, sulfydryl, amino or halogen;

$R_2$ is selected from hydrogen, deuterium or $C_{1-10}$ heteroalkyl, and the $C_{1-10}$ heteroalkyl is optionally substituted or unsubstituted by $C_{1-4}$ alkyl, $C_{1-4}$ alkoxyl, $C_{1-4}$ alkylthio, cyano, nitro, hydroxyl, sulfydryl, amino or halogen; $R_3$ is selected from hydrogen, deuterium or $C_{1-10}$ heteroalkyl, and the $C_{1-10}$ heteroalkyl is optionally substituted or unsubstituted by $C_{1-4}$ alkyl, $C_{1-4}$ alkoxyl, $C_{1-4}$ alkylthio, cyano, nitro, hydroxyl, sulfydryl, amino or halogen;

Z is selected from one of the following fragments:

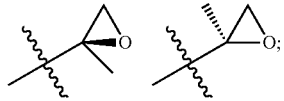

and

P is selected from hydrogen, $C_{1-10}$ alkyl, $C_{1-10}$ alkoxyl, aryl or heteroaryl; and the $C_{1-10}$ alkyl, $C_{1-10}$ alkoxyl, aryl or heteroaryl is optionally substituted or unsubstituted by $C_{1-4}$ alkyl, $C_{1-4}$ alkoxyl, halogen or halogenated $C_{1-4}$ alkyl.

Preferably:
$R_1$ is selected from hydrogen, $C_{1-10}$ alkyl, phenyl, naphthyl, indolyl, thiazolyl, thienyl, benzothienyl, imidazolyl or benzyl, and the $C_{1-10}$ alkyl, phenyl, naphthyl, indolyl, thiazolyl, thienyl, benzothienyl, imidazolyl or benzyl is optionally substituted or unsubstituted by $C_{1-4}$ alkyl, $C_{1-4}$ alkoxyl, cyano, nitro, hydroxyl, sulfydryl, amino or halogen;

$R_2$ is selected from hydrogen or $C_{1-10}$ heteroalkyl, and the $C_{1-10}$ heteroalkyl is optionally substituted or unsubstituted by $C_{1-4}$ alkyl, $C_{1-4}$ alkoxyl or $C_{1-4}$ alkylthio;

$R_3$ is selected from hydrogen or $C_{1-10}$ heteroalkyl, and the $C_{1-10}$ heteroalkyl is optionally substituted or unsubstituted by $C_{1-4}$ alkyl, $C_{1-4}$ alkoxyl or $C_{1-4}$ alkylthio; and P is selected from hydrogen, morpholinyl, methylisoxazolyl, 2-methylthiazolyl, 2,5-dichlorophenyl or pyrazinyl.

Further preferably:
$R_1$ is selected from hydrogen, $C_{1-4}$ alkyl, phenyl, indolyl, thiazolyl, thienyl, benzothienyl, imidazolyl or benzyl, and the $C_{1-4}$ alkyl, phenyl, indolyl, thiazolyl, thienyl, benzothienyl, imidazolyl or benzyl is optionally substituted or unsubstituted by $C_{1-4}$ alkyl, $C_{1-4}$ alkoxyl, nitro or halogen;

$R_2$ is selected from hydrogen or $C_{1-4}$ heteroalkyl, and the $C_{1-4}$ heteroalkyl is optionally substituted or unsubstituted by $C_{1-4}$ alkyl, $C_{1-4}$ alkoxyl or $C_{1-4}$ alkylthio; and $R_3$ is selected from hydrogen or $C_{1-4}$ heteroalkyl, and the $C_{1-4}$ heteroalkyl is optionally substituted or unsubstituted by $C_{1-4}$ alkyl, $C_{1-4}$ alkoxyl or $C_{1-4}$ alkylthio.

The term "alkyl" is used to indicate a saturated hydrocarbon group, $C_{1-10}$ alkyl refers to a saturated hydrocarbon group containing 1-10 carbon atoms, and $C_{1-4}$ alkyl refers to a saturated hydrocarbon group containing 1-4 carbon atoms.

The term "C$_{1-10}$ heteroalkyl" refers to a saturated alkyl group having 1-10 carbon atoms and containing S, O or N atoms in the alkyl chain.

The term "cycloalkyl" refers to non-aromatic carbocyclic groups, including cyclized alkyl groups. Cycloalkyl may include bicyclic or polycyclic systems. Examples of cycloalkyl include cyclopropyl, cyclobutyl, cyclopentyl, cyclohexyl and cycloheptyl. The C$_{3-6}$ cycloalkyl refers to cycloalkyl groups containing 3-6 carbon atoms.

The term "heterocycloalkyl" refers to non-aromatic heterocarbocyclic groups, including cyclized alkyl groups in which one or more ring-forming carbon atoms are substituted by heteroatoms such as O, N or S atoms. The heterocycloalkyl preferably has 3, 4, 5, 6 or 7 ring-forming atoms.

The term "heteroaryl" refers to aromatic heterogroups containing heteroatoms O, N or S, such as furyl, thienyl, benzothienyl, pyrrolyl, thiazolyl, oxazolyl, imidazolyl, pyridyl, pyridazinyl, pyrimidinyl, pyrazinyl, quinolinyl, isoquinolinyl, indolyl, benzofuranyl, purinyl and acridinyl.

"Alkoxyl" refers to —O-alkyl groups which generally have 1-10 carbon atoms. Examples of alkoxyl include methoxy, ethoxy, propoxy (e.g., n-propoxy and isopropoxy) and t-butoxy.

"Alkylthio" refers to —S-alkyl groups which generally have 1-10 carbon atoms. Examples of alkylthio include methylthio, ethylthio, propylthio (e.g., n-propylthio and isopropylthio) and t-butylthio.

"Aryl" refers to aromatic carbocyclic groups, including monocyclic or polycyclic aromatic hydrocarbons such as phenyl, naphthyl, anthryl and phenanthryl.

"Aryloxy" refers to —O-aryl, and the concept of aryl is as described above. The most preferred example of aryloxy is phenoxy.

"Halogen" includes fluorine, chlorine, bromine, and iodine.

The amino acids substituted by the R$_1$, R$_2$ and R$_3$ groups in the compound of the present invention may be racemates or have optical activity. The amino acids substituted by the R$_1$, R$_2$ and R$_3$ groups in the present invention are preferably in the S configuration.

In the description of the present invention, when a group is substituted or unsubstituted by a substituent, it means that the group is a substituted or unsubstituted group. When the group is a substituted group, the substituent is one or more of the substituents. For example, the C$_{1-10}$ alkyl being optionally substituted or unsubstituted by C$_{1-4}$ alkyl, C$_{1-4}$ alkoxyl, C$_{1-4}$ alkylthio, cyano, nitro, hydroxyl, sulfydryl, amino or halogen, means the C$_{1-10}$ alkyl is substituted or unsubstituted C$_{1-10}$ alkyl, and the substituted C$_{1-10}$ alkyl refers to C$_{1-10}$ alkyl of which the substituent is one or more of C$_{1-4}$ alkyl, C$_{1-4}$ alkoxyl, C$_{1-4}$ alkylthio, cyano, nitro, hydroxyl, sulfydryl, amino or halogen.

More preferably, the tripeptide propylene oxide derivative is selected from the following:

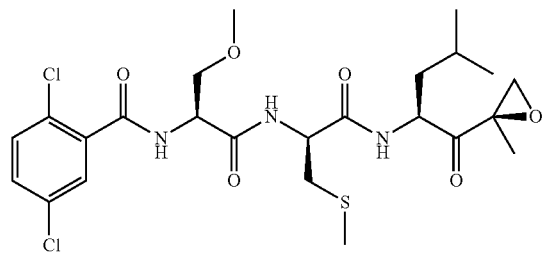

,

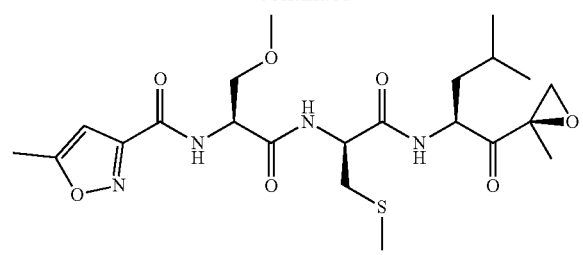

,

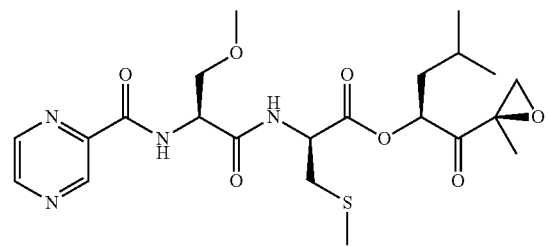

,

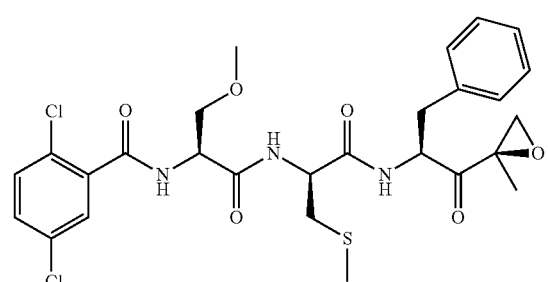

,

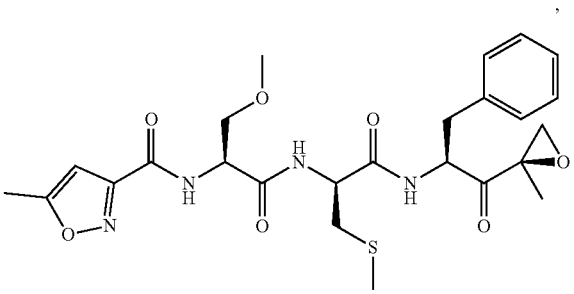

,

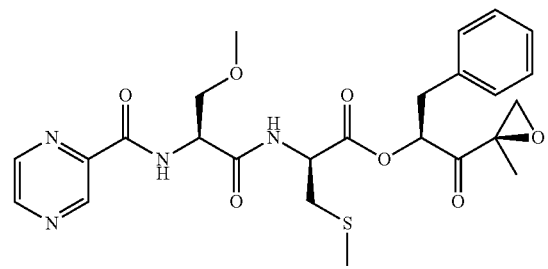

,

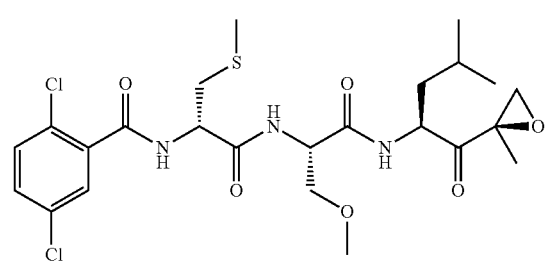

,

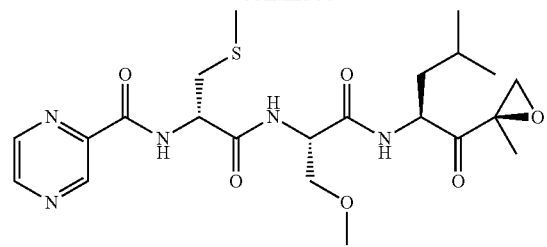
,
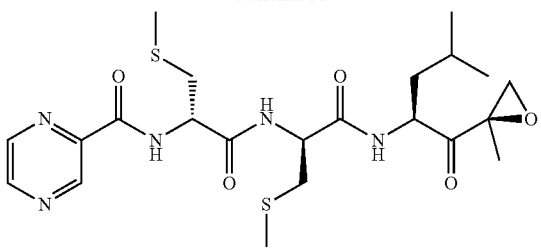
,
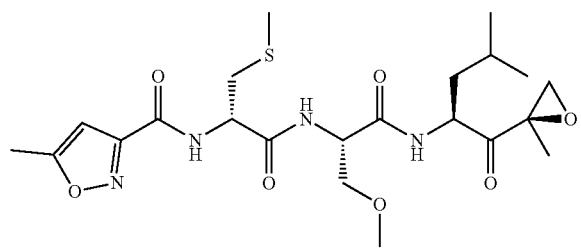
,
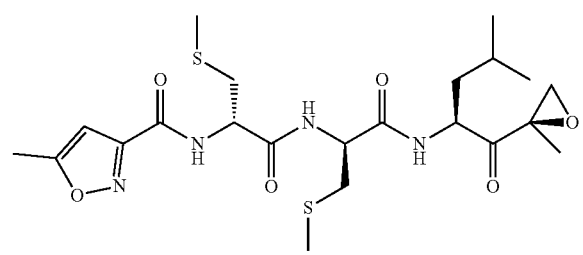
,
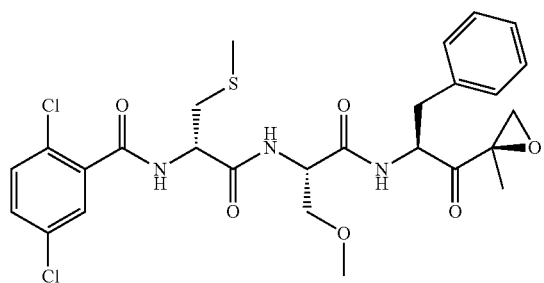
,
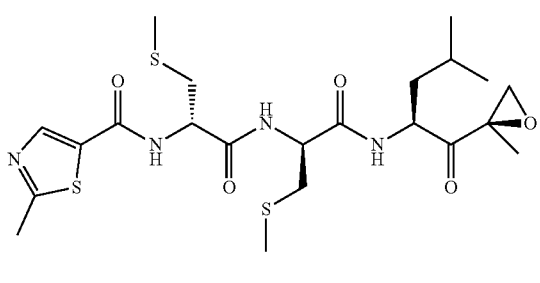
,
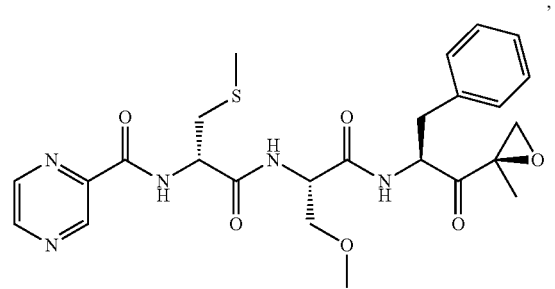
,
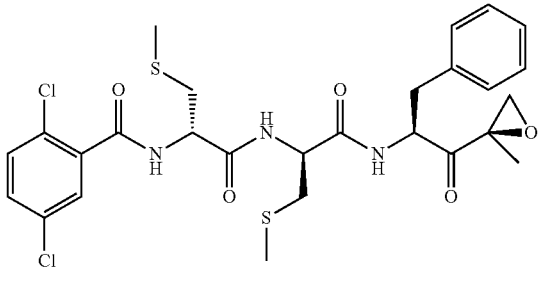
,
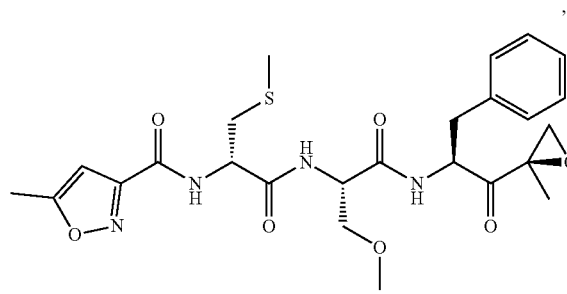
,
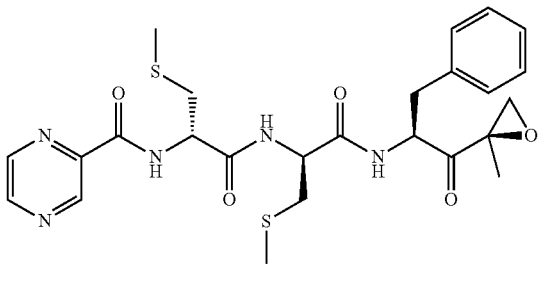
,
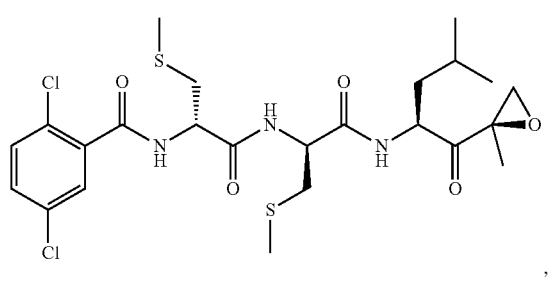
,
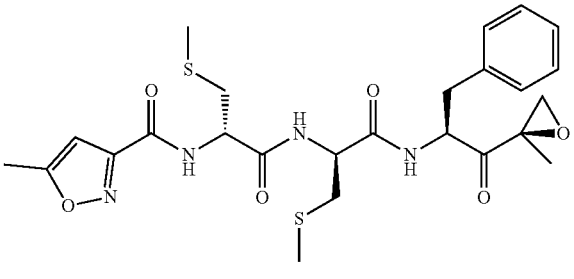
,

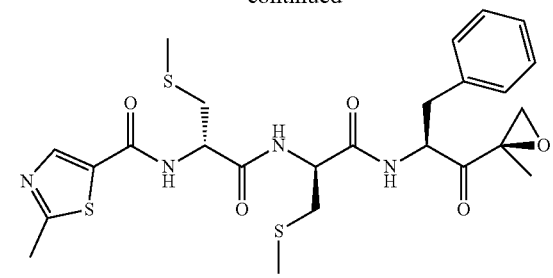
,
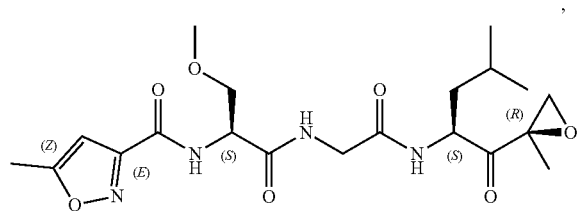
,
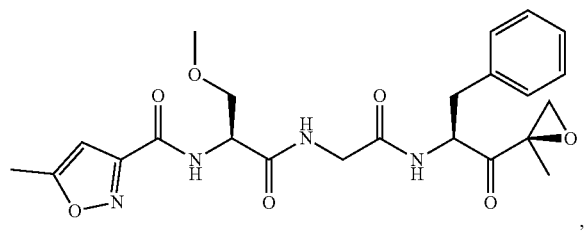
,
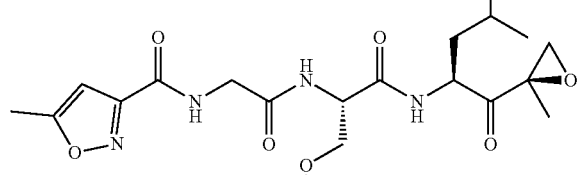
,
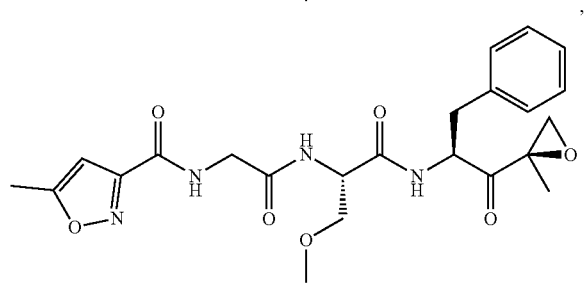
,
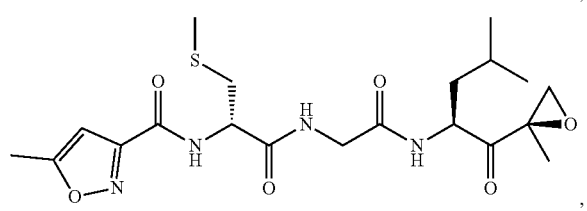
,
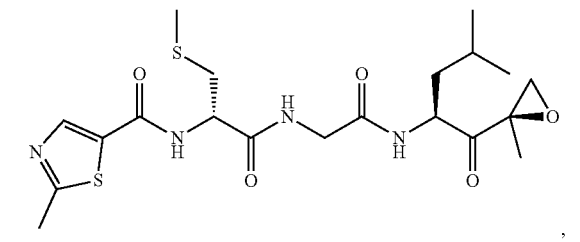
,
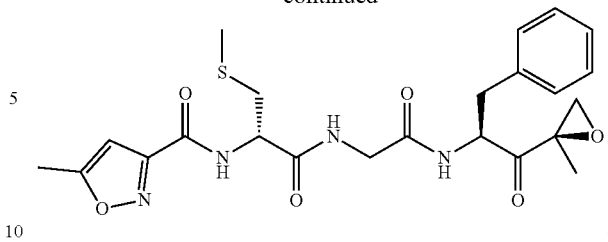
According to the preparation method of the tripeptide propylene oxide derivative or pharmaceutically acceptable salt thereof, the tripeptide propylene oxide derivative or pharmaceutically acceptable salt thereof is synthesized according to the following route:
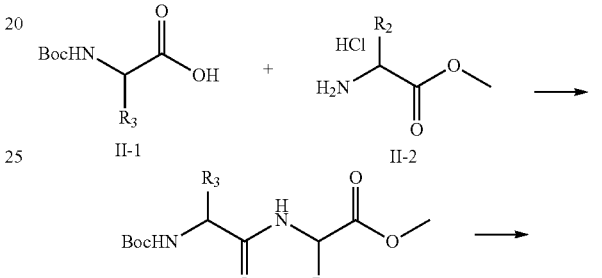

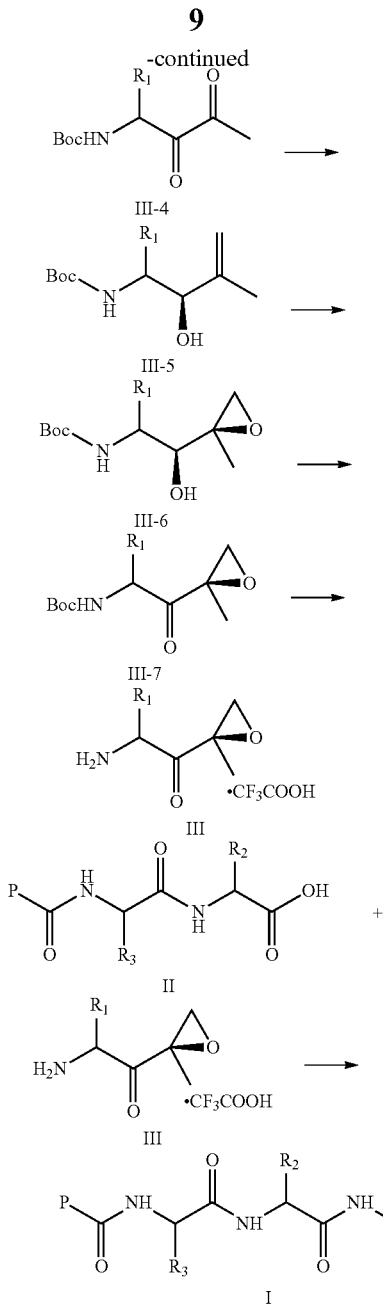

The definitions of the groups P, $R_1$, $R_2$, $R_3$ and Z in the reaction formula are as described above. Formulae (II-1) and (II-2) react under the action of a condensing agent to obtain formula (II-3). Formula (II-3) produces (II-4), under the action of trifluoroacetic acid. Formula (II-4) reacts with carboxylic acid substituted by the P group under the action of a peptide condensing agent to produce formula (II-6), and formula (II-6) produces (II) under the action of LiOH and water.

The preparation method of the compound of the present invention is detailed below:

The definitions of P, $R_1$, $R_2$, $R_3$ and Z are as described above.

The preparation method of the compound (II) includes the following steps:

1) The amino acid of the structure of formula (II-1) and the amino acid methyl ester of the structure of formula (II-2) produce the compound of the structure of formula (II-3) under the action of a condensing agent.

2) After the compound of formula (II-3) is dissolved in DCM, trifluoroacetic acid is added to react to produce a compound of the structure of formula (II-4).

3) The compound of the structure of formula (II-4) and the compound (II-5) are condensed under the action of the condensing agent to produce the compound of the structure of formula 4) The compound of the structure of formula (II-6) is saponified to obtain the compound of the structure of (II).

Finally, the compounds (II) and (III) react to produce (I) in the presence of a certain condensing agent. The condensing agent used is 1-ethyl-3-(3-dimethylaminopropyl)carbodiimide hydrochloride (abbreviated as EDC·HCl), or benzotriazol-1-yl-oxytripyrrolidinophosphonium hexafluorophosphate (abbreviated as PYBOP), or 1-hydroxybenzotriazole (abbreviated as HOBt).

A pharmaceutical composition is provided, and the composition includes the tripeptide propylene oxide derivative or pharmaceutically acceptable salt thereof according to claim 1 and a pharmaceutically acceptable carrier.

Application of the tripeptide propylene oxide derivative or pharmaceutically acceptable salt thereof or the composition in preparation of a proteasome inhibiting drug is provided.

Application of the tripeptide propylene oxide derivative or pharmaceutically acceptable salt thereof or the composition in preparation of drugs for treating inflammation, cancer or hyperproliferative diseases is provided.

Application of the tripeptide propylene oxide derivative or pharmaceutically acceptable salt thereof or the composition in preparation of drugs for treating immune-related diseases is provided.

Application of the tripeptide propylene oxide derivative or pharmaceutically acceptable salt thereof or the composition in preparation of drugs changing various antigen peptides produced by proteasome in organisms is provided.

Application of Enzyme Inhibitors

According to reports, there are many biological effects of proteasome inhibition at the cellular level. After cells are treated with various proteasome inhibitors, accumulation of polyubiquitinated proteins, changes in cell morphology and cell apoptosis occur. Inhibition of the proteasome has also been suggested as a potential anti-tumor treatment strategy. In the screening of anti-tumor compounds, epoxomicin is first identified, confirming that the proteasome is a target of anti-tumor chemotherapy drugs. Therefore, the compounds can be used to treat cancer. The inhibition of the proteasome is further linked with inhibition of NF-κB activation and stabilization of p53 levels. Therefore, the compounds of the present invention can also be used to inhibit NF-κB activation and stabilize the p53 levels in cell culture. Since NF-κB is a key regulatory factor of inflammation, NF-κB is an attractive target for anti-inflammatory therapeutic intervention. Therefore, the compounds of the present invention can be used to treat chronic inflammation-related diseases, including but not limited to COPD, psoriasis, bronchitis, emphysema and cystic fibrosis.

The compounds disclosed in the present invention can be used to treat diseases (such as muscle disuse) directly mediated by the proteolytic function of the proteasome or diseases indirectly mediated by proteins (such as NF-κB) processed by the proteasome. The proteasome is involved in rapid elimination and post-translational processing of proteins (such as enzymes) involved in cell regulation (such as cell cycle, gene transcription and metabolic pathways), intercellular communication, and immune response (such as antigen presentation). Specific examples described below include: β-amyloid and regulatory proteins such as cyclin, TGF-β and transcription factor NF-κB.

Other embodiments of the present invention relate to cachexia and muscular dystrophy. The proteasome degrades many proteins in mature reticulocytes and growing fibroblasts. In cells lacking insulin or serum, the rate of proteolysis almost doubles. Inhibition of the proteasome can reduce the proteolysis, thereby reducing muscle protein loss and kidney or liver nitrogen load. The inhibitor of the present invention can be used to treat diseases such as cancer, chronic infectious diseases, fever, muscle disuse (atrophy), and renal failure, diabetes and liver failure related to denervation, nerve damage, fasting and acidosis. See, for example, Goldberg's U.S. Pat. No. 5,340,736. Therefore, embodiments of the present invention include the following methods: reducing the rate of muscle protein degradation of cells; reducing the rate of intracellular protein degradation; reducing the rate of p53 protein degradation of cells; and inhibiting the growth of p53-related cancers. The above methods all involve contacting cells (in vivo or in vitro, e.g., a patient's muscle) with an effective amount of a compound (e.g., a pharmaceutical composition) of the present invention.

Another protein processed by the proteasome is NF-κB, a member of the Rel protein family. Transcriptional activating proteins of the Rel family can be divided into two groups. The first group requires proteolytic processing, including p50 (NF-κB1, 105 kDa) and p52 (NF-κ2, 100 kDa). The second group does not require proteolytic processing, including p65 (RelA, Rel (c-Rel) and RelB). Both homodimers and heterodimers can be formed by members of the Rel family; for example, NF-κB is a p50-p65 heterodimer. After phosphorylation and ubiquitination of IκB and p105, the two proteins are respectively degraded and processed to produce active NF-κB, which is transported from the cytoplasm to the nucleus. Ubiquitinated p105 is also processed by purified proteasomes (Palombella et al., Cell (1994) 78:773-785). Active NF-κB forms a stereospecific enhancer complex with other transcriptional activators and, e.g. HMGI (Y), and induces selective expression of specific genes.

NF-κB regulates genes involved in immunity, inflammatory reaction, and mitotic events. For example, the expression of immunoglobulin light chain κ genes, IL-2 receptor a chain genes, class I major histocompatibility complex genes, and many cytokine genes coding IL-2, IL-6, granulocyte colony stimulating factors and IFN-β requires NF-κB (Palombella et al., Cell (1994) 78:773-785). Some embodiments of the present invention include methods for affecting the expression levels of IL-2, MHC-I, IL-6, TNFα, IFN-β, or any other aforementioned protein, each method including administering an effective amount of a compound of the present disclosure to the patient. A complex including p50 is a rapid mediator of acute inflammatory reaction and immune response (Thanos, D. and Maniatis, T., Cell (1995) 80:529-532).

NF-κB is also involved in expression of cell adhesion genes coding E-selectin, P-selectin, ICAM and VCAM-1 (Collins, T., Lab. Invest. (1993) 68:499-508). One embodiment of the present invention is a method for inhibiting cell adhesion (for example, E-selectin, P-selectin, ICAM or VCAM-1 mediated cell adhesion). The method includes contacting the cells with an effective amount of the compound (or pharmaceutical composition) of the present invention, or administering an effective amount of the compound (or pharmaceutical composition) of the present invention to the patient.

Intracellular proteolysis produces small peptides for presentation to T lymphocytes, thereby inducing class I MHC-mediated immune response. The immune system screens autologous cells that have been infected by viruses or that have undergone cancer transformation. One embodiment is a method for inhibiting antigen presentation of cells, and the method includes contacting the cells with a compound of the present invention. The compound of the present invention can be used to treat immune-related diseases, such as allergy, asthma, organ/tissue rejection (graft versus host disease) and autoimmune diseases, including but not limited to lupus, rheumatoid arthritis, psoriasis, multiple sclerosis, and inflammatory bowel diseases (such as ulcerative colitis and Crohn's disease). Therefore, another embodiment is a method of inhibiting the immune system of a patient (e.g., inhibiting transplant rejection, allergy, autoimmune diseases, and asthma), and the method includes administering an effective amount of a compound of the present invention to the patient.

Yet another embodiment is a method of changing an antigen peptide library produced by proteasome or other Ntn with multi-catalytic activity. For example, if the PGPH activity of the 20S proteasome is selectively inhibited, the group of antigen peptides produced by the proteasome and presented on the cell surface with MHC molecules is not the same as the group of antigen peptides generated and presented under any one of conditions without any enzyme inhibition or, e.g., the chymotrypsin-like activity of the proteasome is selectively inhibited.

Certain proteasome inhibitors block the degradation and processing of ubiquitinated NF-κB in vitro and in vivo. Proteasome inhibitors also block IκB-α degradation and NF-κB activation (Palombella et al., Cell (1994) 78:773-785; Traenckner) et. (EMBO J. (1994) 13:5433-5441). One embodiment of the present invention is a method of inhibiting IκB-α degradation, and the method includes contacting cells with a compound of the present invention. Another embodiment is a method of reducing the cell content of NF-κB in cells, muscles, organs or patients, and the method includes contacting the cells, muscles, organs, or patients with the compound of the present invention.

Other eukaryotic transcription factors that require proteolytic processing include general transcription factor TFIIA, herpes simplex virus VP16 accessory protein (host cytokine), virus-inducible IFN regulatory factor 2 protein, and membrane-bound sterol regulatory element binding protein 1.

Another embodiment of the present invention is a method of influencing the cyclin-dependent eukaryotic cell cycle, and the method includes contacting cells (in vitro or in vivo) with a compound of the present invention. Cyclin is involved in cell cycle regulation. The proteasome is involved in the degradation of cyclin. Examples of cyclins include mitotic cyclin, G1 cyclin and cyclin B. The degradation of cyclins allows the cell to exit one phase of the cell cycle (e.g., mitosis) and enter another phase (e.g., division). It is believed that all cyclins are associated with p34.sup.cdc2 protein kinase or related kinases. The proteolytic targeting signal is located at amino acid 42-RAAL-GNISEN-50 (degradation box). There is evidence that cyclin is converted into a form that is easily destroyed by ubiquitin ligase, or that cyclin-specific ligase is activated during mitosis (Ciechanover, A., Cell, (1994) 79:13-21). Inhibition of the proteasome can inhibit cyclin degradation, thereby inhibiting cell proliferation in, for example, cyclin-related cancers (Kumatori et al., Proc. Natl. Acad. Sci. USA (1990) 87:7071-7075). One embodiment of the present invention is a method for treating proliferative diseases (such as cancer, psoriasis, or restenosis) in patients, and the method includes administering an effective amount of a compound of the present invention to the patients. The present invention also includes a method for treating cyclin-related inflammation in patients, and the method includes administering a therapeutically effective amount of a compound of the present invention to the patients.

Other embodiments are methods of influencing proteasome-dependent regulation of oncogene proteins and methods for treating or inhibiting cancer growth. Each method includes contacting cells (in vivo, for example, in a patient, or in vitro) with a compound of the present invention. HPV-16 and HPV-18 derived E6 proteins stimulate ATP- and ubiquitin-dependent conjugation and degradation of p53 in crude reticulocyte lysates. It has been confirmed that the recessive oncogene p53 accumulates at non-permissible temperatures in cell lines with mutant heat-labile E1. High levels of p53 may cause cell apoptosis. Examples of proto-oncogene proteins degraded by the ubiquitin system include c-Mos, c-Fos and c-Jun. One embodiment is a method for treating p53-related cell apoptosis, and the method includes administering an effective amount of a compound of the present invention to a patient.

Finally, the compounds of the present invention can also be used as diagnostic reagents (e.g., in diagnostic kits or clinical laboratories) for screening proteins (e.g., enzymes, transcription factors) processed by Ntn hydrolase (including proteasome). The compounds of the present invention can also be used as research reagents to specifically bind to an X/MB 1 subunit or a chain and inhibit the proteolytic activity related thereto. For example, the activity of other subunits of the proteasome (and specific inhibitors thereof) can be determined.

Most cellular proteins undergo proteolytic processing during maturation or activation. The enzyme inhibitors disclosed herein can be used to determine whether cellular, developmental, or physiological processes or output is regulated by the proteolytic activity of a specific Ntn hydrolase. One such method includes: obtaining an organism, a whole cell preparation or a cell extract; contacting the organism, the cell preparation or the cell extract with a compound of the present invention; and enabling the organism, the cell preparation or the cell extract contacted with the compound of the present invention to signal, and then monitoring the process or output. High selectivity of the compounds of the present invention allows rapid and accurate elimination or influence of Ntn (such as 20S proteasome) in specific cellular, developmental, or physiological processes.

Administration

Depending on the disease to be treated and the age, health and weight of the patient, the compounds prepared according to the methods described herein can be administered in various forms, which are well known in the art. For example, when the compounds are ready for oral administration, the compounds can be formulated as tablets, capsules, granules, powders, or syrups; or when used for parenteral administration, the compounds can be formulated as an injection (intravenous, intramuscular, or subcutaneous), infusion preparation or suppository. When administered by the ocular mucosal route, the compounds can be formulated as eye drops or ointment. These preparations can be prepared by conventional methods, and if necessary, the active ingredients can be mixed with any conventional additives or excipients (e.g. binders, disintegrants, lubricants, flavoring agents, solubilizers, suspending agents, emulsifiers, coating agents, cyclodextrins and/or buffering agents). Although the dosage depends on the patient's symptoms, age and weight, the nature and severity of the disease to be treated or prevented, the route of administration and the form of the drug, generally, the recommended daily dose of the compounds of the present invention for adult patients is 0.01 mg-2000 mg, which can be administered as a single dose or multiple divided doses. The amount of the active ingredient mixed with the carrier to prepare a single dosage form is usually the amount of the compound that can produce a therapeutic effect.

In terms of the therapeutic effect on a particular patient, the precise administration time and/or composition dosage to obtain the best therapeutic effect depends on the activity, pharmacokinetics and bioavailability of the specific compound, the physiological conditions (including age, gender, disease type and stage, general physical condition, response to a specific dose, and drug type) of the patient, the route of administration, etc. In any case, the above criteria can be used as the basis for accurate adjustment of therapy, e.g., determining the optimal administration time and/or dosage, which only requires routine experimentation, including monitoring the patient and adjusting the dosage and/or administration time.

The term "pharmaceutically acceptable" as used herein refers to those ligands, raw materials, compositions and/or dosage forms that, within the scope of reasonable medical judgment, are suitable for contact with human tissues and animal tissues, have no excessive toxicity, irritation, allergies or other problems or complications, and have a reasonable benefit/risk ratio.

The term "pharmaceutically acceptable carrier" as used herein refers to a pharmaceutically acceptable raw material, ingredient or solvent, such as a liquid or solid filler, diluent, excipient, solvent or encapsulating material. All carriers must be "acceptable", that is, compatible with the other preparation ingredients of the preparation, and not harmful to the patient. Some examples of the pharmaceutically acceptable carriers include: (1) sugars such as lactose, glucose and sucrose; (2) starches such as corn starch, potato starch and substituted or unsubstituted β cyclodextrin; (3) cellulose and derivatives thereof, such as sodium carboxymethyl cellulose, ethyl cellulose and cellulose acetate; (4) powdered tragacanth; (5) malt; (6) gelatin; (7) talc; (8) excipients, such as cocoa butter and suppository wax; (9) oil, such as peanut oil, cotton seed oil, safflower oil, sesame oil, olive oil, corn oil and soybean oil; (10) dihydric alcohols, such as propylene glycol; (11) polyols, such as glycerol, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethanol; (20) phosphate buffer solution; and (21) other non toxic compatible substances used in pharmaceutical preparations. In certain embodiments, the pharmaceutical composition of the present invention is non-pyrogenic, that is, cause no significant increase in body temperature after administration to a patient.

The term "pharmaceutically acceptable salt" refers to the relatively non-toxic inorganic acid addition salt and organic acid addition salt of the inhibitor. These salts can be prepared in situ during the final isolation and purification of the inhibitor, or the purified inhibitor in the free base form can be separately reacted with a suitable organic or inorganic acid, and then the salt formed thereby can be isolated. Representative salts include hydrobromide, hydrochloride, sulfate, bisulfate, nitrate, acetate, pentanoate, oleate, palmitate, stearate, laurate, benzoate, lactate, phosphate, tosylate, citrate, maleate, fumarate, succinate, tartrate, naphthylate, methanesulfonate, glucoheptonate, lactobionate, laurylsulfonate and amino acid salts (See, for example, Berge et al., (1977) "Pharmaceutical Salts", J. Pharm. Sci. 66:1-19).

In other cases, the inhibitor used in the methods of the present invention may contain one or more acidic functional groups and, therefore, can form a pharmaceutically acceptable salt with a pharmaceutically acceptable base. In these cases, the term "pharmaceutically acceptable salt" refers to the relatively non-toxic inorganic base addition salt and organic base addition salt of the inhibitor. These salts can also be prepared in situ during the final isolation and purification of the inhibitor, or the purified inhibitor in the free acid form can be separately reacted with a suitable base (for example, the hydroxide, carbonate or bicarbonate of a pharmaceutically acceptable metal cation), ammonia or pharmaceutically acceptable organic primary, secondary or tertiary amine. Representative alkali metal salts or alkali earth metal salts include lithium salts, sodium salts, potassium salts, calcium salts, magnesium salts and aluminum salts. Representative organic amines that can be used to form alkali addition salts include ethylamine, diethylamine, ethylenediamine, ethanolamine, diethanolamine and piperazine (see, for example, Berge et al., supra).

Wetting agents, emulsifiers and lubricants (such as sodium lauryl sulfate and magnesium stearate) as well as coloring agents, releasing agents, coating agents, sweeteners, flavoring agents, flavor enhancers, preservatives and antioxidants may also be added to the composition.

Examples of pharmaceutically acceptable antioxidants include: (1) water-soluble antioxidants, such as ascorbic acid, cysteine hydrochloride, sodium bisulfate, sodium metabisulfite, sodium sulfite, etc.; (2) oil-soluble antioxidants, such as vitamin C palmitate, butylated hydroxyanisole (BHA), butylated hydroxytoluene (BHT), lecithin, propyl gallate and α-tocopherol; and (3) metal chelating agents, such as citric acid, ethylenediaminetetraacetic acid (EDTA), sorbitol, tartaric acid and phosphoric acid.

Preparations suitable for oral administration can be capsules, cachets, pills, tablets, lozenges (using a flavored matrix, usually sucrose and gum arabic or tragacanth), powders, granules, or a solution or suspension in an aqueous or non-aqueous liquid, or an oil-in-water or water-in-oil liquid emulsion, or an elixir or syrup, or pastilles (using an inert matrix such as gelatin and glycerol, or sucrose and gum arabic) and/or a collutory, etc. All dosage forms contain a predetermined amount of inhibitor as the active ingredient. The composition can also be administered as boluses, granules or paste.

In oral solid dosage forms (capsules, tablets, pills, lozenges, powders, granules, etc.), the active ingredient is mixed with one or more pharmaceutically acceptable carriers, such as sodium citrate or dicalcium phosphate and/or any of the following carriers: (1) fillers or extenders, such as starch, cyclodextrin, lactose, sucrose, glucose, mannitol and/or silicic acid; (2) binders, such as carboxymethyl cellulose, alginate, gelatin, polyvinylpyrrolidone, sucrose and/or gum arabic; (3) humectants, such as glycerol; (4) disintegrants, such as agar, calcium carbonate, potato starch, tapioca starch, alginic acid, certain silicates and sodium carbonate; (5) dissolution retarding agents, such as paraffin; (6) absorption enhancers, such as quaternary ammonium compounds; (7) wetting agents, such as acetol and glyceryl monostearate; (8) adsorbents, such as kaolin and bentonite; (9) lubricants, such as talc, calcium stearate, magnesium stearate, solid polyethylene glycol, sodium lauryl sulfate and mixtures thereof; and (10) coloring agents. In the case of capsules, tablets and pills, the pharmaceutical composition may also contain buffering agents. Similar types of solid compositions may also be used as fillers in soft and hard filled gelatin capsules, using excipients such as lactose or milk candy and high molecular weight polyethylene glycols.

Tablets can be prepared by compression or molding, optionally with one or more auxiliary agents. Compressed tablets can be prepared using binders (such as gelatin or hydroxypropyl methyl cellulose), lubricants, inert diluents, preservatives, disintegrants (such as sodium starch glycolate or croscarmellose sodium), surfactants or dispersants. Molded tablets can be prepared by molding a powdered inhibitor mixture moistened with an inert liquid diluent in a suitable machine.

Tablets and other solid dosage forms (such as lozenges, capsules, pills, and granules) may optionally be notched or prepared with coatings and shells, such as enteric coatings and other coatings well known in the pharmaceutical art. The tablets and other solid dosage forms can also be formulated for sustained or controlled release of active ingredients, using, for example, hydroxypropyl methylcellulose, other polymer matrices, liposomes, and/or microspheres in varying ratios to provide the desired release rate. The tablets and other solid dosage forms can be sterilized by, for example, filtering through a bacterial filter, or incorporating sterilizing agents in a sterile solid form, and the sterilizing agents can be dissolved in sterile water or some other sterile injection media just before use. The compositions may also optionally contain a light-screening agent, or may be a composition that releases the active ingredient only or preferentially in certain parts of the gastrointestinal tract, and optionally adopts a delayed release mode. Examples of embedding compositions that can be used include polymers and waxes. The active ingredient may also be in the form of microcapsules, if appropriate, with one or more of the above excipients.

Oral liquid dosage forms include pharmaceutically acceptable emulsions, microemulsions, solutions, suspensions, syrups and elixirs. In addition to the active ingredients, the liquid dosage form may contain inert diluents commonly used in the art, such as water or other solvents, solubilizers and emulsifiers, such as ethanol, isopropanol, ethyl carbonate, ethyl acetate, benzyl alcohol, benzyl benzoate, propylene glycol, 1,3-butanediol, oils (especially cottonseed oil, peanut oil, corn oil, germ oil, olive oil, castor oil and sesame oil), glycerol, tetrahydrofuranol, polyethylene glycol, fatty acid ester of sorbitan, and mixtures thereof.

In addition to inert diluents, the oral composition may contain adjuvants such as wetting agents, emulsifying agents, suspending agents, sweetening agents, flavoring agents, coloring agents, odorants, and preservatives.

In addition to the active ingredients, the suspension may contain suspending agents, for example, ethoxylated isostearyl alcohol, polyoxyethylene sorbitol and sorbitan esters, microcrystalline cellulose, aluminum metahydroxide, bentonite, agar, tragacanth and mixtures thereof.

Preparations for rectal or vaginal administration can be suppositories, and the suppositories can be prepared by mixing one or more inhibitors with one or more non-irritating suitable excipients or carriers. The excipients or carriers include, for example, cocoa butter, polyethylene glycol, wax for suppositories, or salicylate, which are solid at room temperature and liquid at body temperature, and thus melt in the rectum or vaginal canal and release the active agent.

Preparations suitable for vaginal administration also include vaginal suppositories, tampons, creams, gels, pastes, foams or sprays, and the preparations contain suitable carriers known in the art.

The dosage forms for topical or transdermal administration of inhibitors include powders, sprays, ointments, pastes, creams, lotions, gels, solutions, patches, and inhalants. The active ingredient can be mixed with a pharmaceutically acceptable carrier and any necessary preservatives, buffering agents or propellants under sterile conditions.

In addition to inhibitors, ointments, pastes, creams, and gels can contain excipients, such as animal and vegetable fats, oils, waxes, paraffins, starches, tragacanth, cellulose derivatives, polyethylene glycol, silicone, bentonite, silicic acid, talc, zinc oxide, or mixtures thereof.

In addition to inhibitors, powders and sprays can contain excipients, such as lactose, talc, silicic acid, aluminum hydroxide, calcium silicate, polyamide powder, or mixtures thereof. Sprays may also contain commonly used propellants, such as chlorofluorocarbons and volatile unsubstituted hydrocarbons, such as butane and propane.

Inhibitors can also be administered in the form of aerosols, which can be achieved by preparing an aqueous aerosol, a liposome preparation or solid particles containing the composition. Non-aqueous (e.g. a fluorocarbon propellant) suspensions can be used. Sonic nebulizers are preferred because they can minimize the shear force that can cause degradation of the compound.

Generally, an aqueous aerosol is prepared by formulating an aqueous solution or suspension of the drug together with conventional pharmaceutically acceptable carriers and stabilizers. The carriers and stabilizers vary according to the requirements of the specific composition, but usually include non-ionic surfactants (Tween, Pluronic, sorbitan esters, lecithin and Cremophor), pharmaceutically acceptable co-solvents (such as polyethylene glycol), harmless proteins (such as serum albumin), oleic acid, amino acids (such as glycine), buffering agents, salts, sugars or sugar alcohols. Aerosols are usually prepared with isotonic solutions.

Transdermal patches have more advantages in controlling the administration of inhibitors to the body. Such dosage forms can be prepared by dissolving or dispersing the drug in a suitable medium. Absorption enhancers can also be used to increase the flux of the inhibitor through the skin. Such a migration rate can be controlled by a rate regulating membrane, or by dispersing the inhibitor into a polymer matrix or gel.

The pharmaceutical composition of the present invention suitable for parenteral administration contains one or more inhibitors and one or more pharmaceutically acceptable sterile aqueous or non-aqueous solutions, dispersions, suspensions or emulsions, or sterile powder that can be reconstituted into a sterile injection solution or dispersion before use, which may contain antioxidants, buffering agents, bacteriostatic agents, solutes that make the preparation isotonic with the blood of the intended recipient, suspending agents or thickening agents.

Examples of suitable aqueous and non-aqueous carriers that can be used in the pharmaceutical composition of the present invention include water, ethanol, polyols (such as glycerol, propylene glycol and polyethylene glycol), suitable mixtures thereof, vegetable oils (such as olive oil) and organic esters for injection, such as ethyl oleate. Proper fluidity can be maintained, for example, by using a coating material (such as lecithin), maintaining the required particle size for the dispersion, and using a surfactant.

The compositions may also contain adjuvants such as preservatives, wetting agents, emulsifying agents, and dispersing agents. The addition of various antibacterial and antifungal agents can prevent the action of microorganisms, such as parabens, chlorobutanol, phenol and sorbic acid. Tonicity modifiers such as sugar and sodium chloride may also be required in the composition. In addition, the absorption of injectable pharmaceutical preparations can be prolonged by adding reagents (such as aluminum monostearate and gelatin) that delay absorption.

In some cases, in order to prolong the effect of the drug, it is necessary to slow the absorption rate of the drug injected subcutaneously or intramuscularly. For example, the absorption of a parenterally administered drug is delayed by dissolving or suspending the drug in an oil solvent.

An injectable reservoir preparation is prepared by forming a microcapsule matrix of the inhibitor in a biodegradable polymer (such as polylactide-polyglycolide). According to the ratio of the drug to the polymer and the properties of a specific polymer used, the release rate of the drug can be regulated. Examples of other biodegradable polymers include poly(orthoesters) and poly(anhydrides). Reservoir injection preparations can also be prepared by encapsulating the drug in liposomes or microemulsions compatible with body tissues.

The pharmaceutical preparations can be administered orally, parenterally, topically, or rectally. Of course, the pharmaceutical preparations are administered in dosage forms suitable for various administration routes. For example, the pharmaceutical preparations are administered in the form of tablets or capsules, injections, inhalants, eye washes, ointments, suppositories, and infusions, topically administered in the form of lotions or ointments, or rectally administered in the form of suppositories. Oral administration is preferred.

As used herein, the term "parenteral administration" refers to administration methods other than enteral and topical administration, and usually refers to administration by injection and infusion. Injections include but not limited to intravenous, intramuscular, intraarterial, intrathecal, intrasaccular, intraorbital, intracardiac, intradermal, intraperitoneal, transtracheal, subcutaneous, subepidermal, intra-articular, subcapsular, subarachnoid, intraspinal and intrasternal injections.

As used herein, the terms "systemic administration" and "peripheral administration" mean that ligands, drugs, or other substances are not administered directly into the central nervous system, but enter the patient's body and therefore undergo metabolism or other similar processes, such as subcutaneous administration.

The inhibitors can be administered to humans or other animals for therapeutic purposes. Any suitable route of administration can be used, including oral, nasal (e.g., spray), rectal, intravaginal, parenteral, intracisternal and topical administration (e.g., powders, ointments or drops, including buccal and sublingual administration).

No matter which route of administration is chosen, the inhibitor (which can be used in a suitable hydrated form) of the present invention and/or the pharmaceutical composition of the present invention can be formulated into a pharmaceutically acceptable dosage form by conventional methods known in the art.

The actual dosage level of the active ingredient of the pharmaceutical composition of the present invention can be changed, so as to obtain an effective amount of the active ingredient to achieve the desired therapeutic response without poisoning the patient for specific patients, compositions and administration modes.

The concentration of the compounds of the present invention in the pharmaceutically acceptable mixtures varies depending on a plurality of factors, including the dose of the compounds administered, the pharmacokinetic characteristics of the compounds used, and the route of administration. Generally, the composition of the present invention can be provided as an aqueous solution containing about 0.1-10% w/v of the compounds of the present invention for parenteral administration. A typical dose is about 0.01 mg/kg body weight to about 50 mg/kg body weight per day, administered in 1-4 times. Each divided dose may contain the same or different compounds of the present invention. The dose to be administered must be an effective dose, and the effective dose depends on many factors, including the patient's general health, the preparation of the selected compounds, and the route of administration.

Another aspect of the present invention provides a combination therapy in which one or more other therapeutic drugs are administered together with the proteasome inhibitor of the present invention. Such combination therapy can be achieved by administering each component of the treatment simultaneously, sequentially, or separately.

In certain embodiments, the compounds of the present invention are administered in combination with one or more other proteasome inhibitors.

In certain embodiments, the compounds of the present invention are administered in combination with chemotherapeutic drugs. Suitable chemotherapeutic drugs may include natural products such as catharanthus alkaloids (i.e. vinblastine, vincristine and vinorelbine), paclitaxel, epidipodophyllotoxin (i.e. etoposide, teniposide), antibiotics (dactinomycin (actinomycin D), daunorubicin, doxorubicin and idarubicin), anthracyclines, mitoxantrone, bleomycin, plicamycin (mithramycin) and mitomycin, enzyme (L-asparaginase, which systematically metabolizes L-asparagine and eliminates cells that cannot synthesize their own asparagine); antiplatelet drugs; anti-proliferation/anti-mitosis alkylating agents, such as nitrogen mustards (nitrogen mustard, cyclophosphamide and analogs thereof, melphalan, chlorambucil), aziridines and methyl melamines (hexamethyl melamine and thiotepa), alkyl sulfonates (busulfan), nitrosoureas (carmustine (BCNU) and analogs thereof, streptozocin), trazenes-dacarbazinine (DTIC); anti-proliferative/anti-mitotic antimetabolites such as folacins (methotrexate), pyrimidine analogs (fluorouracil, fluorouridine and cytarabine), purine analogs and related inhibitors (mercaptopurine, thioguanine, pentostatin and 2-chlorodeoxyadenosine); aromatase inhibitors (anastrozole, exemestane and letrozole); platinum coordination complexes (cisplatin, carboplatin), procarbazine, hydroxyurea, mitotane, aminoglutethimide; hi stone deacetylase (HDAC) inhibitors (trichostatin, sodium butyrate, apicidan, suberoyl anilide hydroamic acid); and hormones (i.e. estrogen) and hormone agonists, such as luteinizing hormone releasing hormone (LHRH) agonists (goserelin, leuprolide and triptorelin). Other chemotherapeutic drugs may include nitrogen mustard, camptothecin, ifosfamide, tamoxifen, raloxifene, gemcitabine, navelbine, or any analogs or derivatives of the foregoing drugs.

In certain embodiments, the compounds of the present invention are administered in combination with cytokines. The cytokines include, but not limited to interferon-γ, -α and -β, interleukins 1-8, 10 and 12, granulocyte monocyte colony stimulating factor (GM-CSF), TNF-α and -β, and TGF-β.

In certain embodiments, the compounds of the present invention are administered in combination with steroids. Suitable steroids include but not limited to 21-acetoxypregnenolone, alclometasone, algestone, amcinonide, beclomethasone, betamethasone, budesonide, chloroprednisone, clobetasol, clocortolone, cloprednol, corticosterone, cortisone, cortivazol, deflazacort, desonide, desoximetasone, dexamethasone, diflorasone, diflucortolone, difluprednate, glycyrrhetinic acid, fluazacort, flucloronide, flumethasone, flunisolide, fluocinolone, fluocinonide, fluocortin butyl, fluocortolone, fluorometholone, fluperolone acetate, fluprednidene acetate, fluprednisolone, flurandrenolide, fluticasone propionate, formocortal, halcinonide, halobatasol proionate, halometasone, hydrocortisone, loteprednol etabonate, mazipredone, medrysone, meprednisone, methyiprednisolone, mometasone furoate, paramethasone, prednicarbate, prednisolone, prednisolone 25-di ethylaminoacetate, prednisolone sodium phosphate, prednisone, prednisolone valerate, prednylidene, rimexolone, tixocortol, triamcinolone, triamcinolone acetonide, triamcinolone benetonide, triamcinolone hexaacetonide and salts and/or derivatives thereof.

In certain embodiments, the compounds of the present invention are administered in combination with an immunotherapeutic agent. Suitable immunotherapeutic agents include but not limited to MDR modulators (verapamil, valspordar, biricodar, tariquidar, laniquidar), cyclosporin, thalidomide and monoclonal antibodies. The monoclonal antibodies can be naked monoclonal antibodies or conjugated monoclonal antibodies, such as rituximab, tositumomab, alemtuzumab, epratuzumab, ibritumomab, gemtuzumab ozogamicin, bevacizumab, cetuximab, erlotinib and trastuzumab.

Technical Effects

Compared with the prior art, the present invention provides tripeptide epoxy ketone compounds with a novel structure and a function of inhibiting proteasome. As 20S proteasome inhibitors, the tripeptide epoxy ketone compounds can block tumor cell proliferation and induce tumor cell apoptosis, so the tripeptide epoxy ketone compounds can be used for the treatment and prevention of a plurality of human and animal diseases such as malignant tumors, and the effect is significantly better.

DETAILED DESCRIPTION OF THE INVENTION

Figure 1:
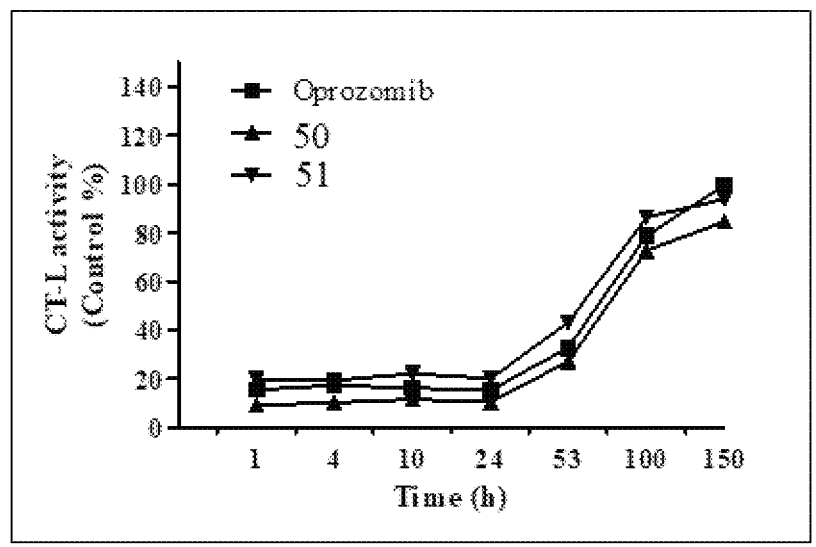
FIG. 1 Results of the pharmacodynamics of the compound of the present invention in ICR mice.

The technical solutions of the present invention are further described below through specific implementations.

Part I Synthesis of Compounds

The compounds of the present invention can be prepared according to the following process:

I. Preparation of the Compound (II)

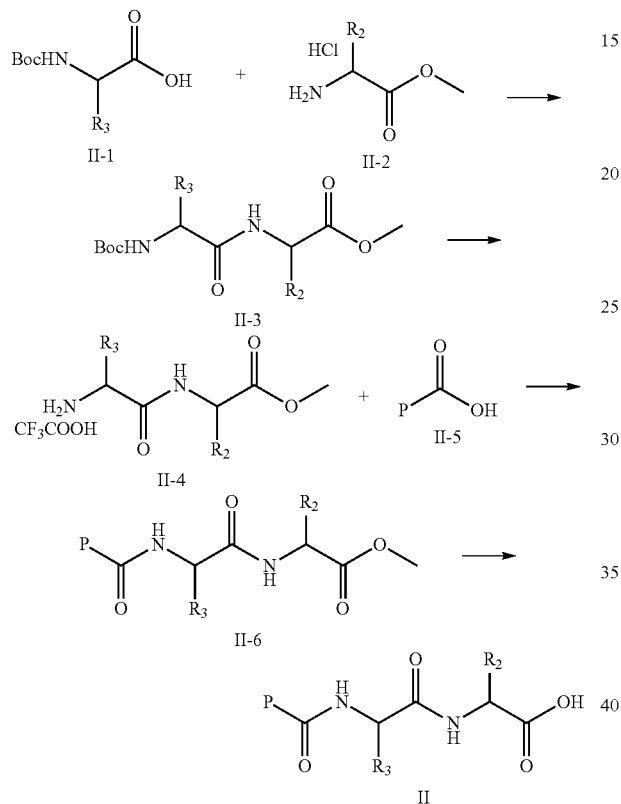

1. Preparation of the Compound (II-3):

The compound (II-1) and HOBt are dissolved in anhydrous DCM and the reaction solution is stirred at −5° C. for 10 min. EDI·HCl is added at the temperature and the reaction solution is stirred for 15-20 min. The compound (II-2) is added and the reaction solution is stirred for 15-20 min. DIPEA is added and the reaction solution is stirred for 20 min. The reaction solution is moved to room temperature for reaction. After the reaction is complete, the reaction solution is poured into water and extracted with DCM. The organic phases are combined and washed with dilute HCl, a NaHCO₃ solution and saturated brine respectively, and dried with anhydrous sodium sulfate. The solvent is evaporated to obtain the compound (II-3).

2. Preparation of the Compound (II-4):

The compound (II-3) is dissolved in anhydrous DCM. TFA is added dropwise slowly at −5° C. After stirring for 0.5 h, the temperature is raised to room temperature and the reaction solution is stirred for 3 h and then tested. After the reaction is complete, the reaction solution is concentrated to obtain brown-red oil. The brown-red oil is slowly added to methyl tert-butyl ether, and the reaction solution is vigorously stirred to obtain a white solid. The white solid is filtered to obtain the compound (II-4).

3. Preparation of the Compound (II-6):

P group substituted carboxylic acid, i.e. the compound (II-5) and HOBt are dissolved in anhydrous DCM and the reaction solution is stirred at −5° C. for 10 min. EDI·HCl is added at the temperature and the reaction solution is stirred for 15-20 min. The compound (II-4) is added and the reaction solution is stirred for 15-20 min. DIPEA is added and the reaction solution is stirred for 20 min. The reaction solution is moved to room temperature for reaction. After the reaction is complete, the reaction solution is poured into water and extracted with DCM. The organic phases are combined and washed with dilute HCl, a NaHCO₃ solution and saturated brine respectively, and dried with anhydrous sodium sulfate. The solvent is evaporated to obtain the compound (II-6).

4. Preparation of the Compound (II):

The compound (II-6) is dissolved in MeOH/H₂O. A LiOH aqueous solution is added dropwise at 0° C. and the reaction solution is stirred for 2 h. The temperature is raised to room temperature for reaction for a certain time. Water is added and the pH is adjusted to 6-7 with hydrochloric acid. The reaction solution is extracted with ethyl acetate. The organic phase is washed with saturated brine, and dried with anhydrous sodium sulfate. The solvent is evaporated to obtain the compound (II).

II. Preparation of the Compound (III)

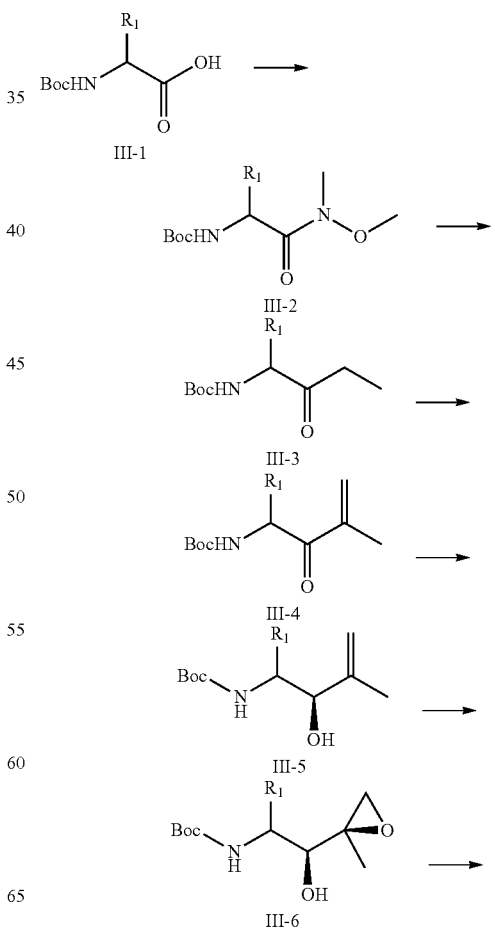

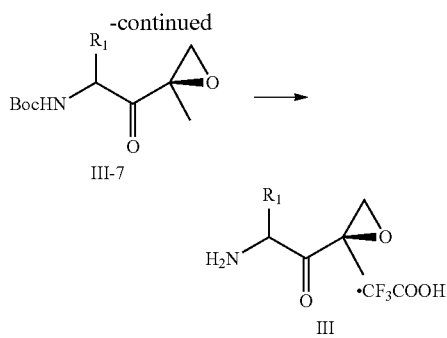

1. Preparation of the Compound (III-2):

The compound (III-1) and HOBt are dissolved in DCM. EDC·HCl is added. After stirring at −5° C. for 15 min, dimethylhydroxylamine hydrochloride is added. DIPEA is added after 15 min. Reaction is performed at low temperature for 25 min. After the reaction is complete at room temperature, the reaction solution is extracted with DCM. The organic phase is washed with 1N HCl, 5% NaHCO$_3$ and saturated brine, and dried with anhydrous sodium sulfate. The solvent is evaporated to obtain the compound (III-2).

2. Preparation of the Compound (III-3):

The compound (III-2) is dissolved with tetrahydrofuran. At −20° C., ethyl magnesium bromide is added dropwise. After dropwise adding, the temperature is raised to room temperature for reaction. After the reaction is complete, 1N HCl is slowly added dropwise to quench the reaction. Extraction is performed with ethyl acetate. The extract is washed with saturated brine. The organic phase is dried and concentrated to obtain the compound (III-3).

3. Preparation of the Compound (III-4):

The compound (III-3) is dissolved with tetrahydrofuran. Piperidine acetate and piperidine are added. Paraformaldehyde is added in batches. After refluxing for 3 h, an appropriate amount of water is added and extraction is performed with ethyl acetate. The extract is washed with 1N HCl and saturated brine respectively. The organic phase is dried and concentrated to obtain the compound (III-4).

4. Preparation of the Compound (III-5):

The compound (III-4) is dissolved in toluene. Aluminum isopropoxide and isopropanol are added. The reaction is performed at 50° C. After the reaction is complete, extraction is performed with water and ethyl acetate. The extract is washed with 1N HCl and saturated brine. The organic phase is dried and concentrated to obtain the compound (III-5).

5. Preparation of the Compound (III-6):

The compound (III-5) is dissolved in DCM. Then vanadium acetylacetonate is added. Under nitrogen protection, the reaction solution is cooled to 0° C. in an ice bath. Tert-Butyl hydroperoxide is slowly added dropwise. After the reaction is complete, an appropriate amount of water is added and extraction is performed with dichloromethane. The extract is washed with saturated sodium thiosulfate and saturated brine respectively. The organic phase is dried, concentrated and purified to obtain the compound (II-6).

6. Preparation of the Compound (III-7):

The compound (III-6) is dissolved in dimethyl sulfoxide. Diisopropylethylamine is added. Pyridine sulfur trioxide is added in batches in an ice bath. The temperature is raised to room temperature for reaction. After the reaction is complete, an appropriate amount of water is added and extraction is performed with ethyl acetate. The extract is washed with 1N HCl and saturated brine. The organic phase is dried and concentrated to obtain the compound (III-7).

7. Preparation of the Compound (III):

The compound (II-7) is dissolved in anhydrous DCM. TFA is slowly added dropwise at −5° C. After stirring for 0.5 h, the temperature is raised to room temperature and the reaction solution is stirred for 3 h and then tested. After the reaction is complete, the reaction solution is concentrated to obtain brown-red oil. The brown-red oil is slowly added to methyl tert-butyl ether, and the reaction solution is vigorously stirred to obtain a white solid. The white solid is filtered to obtain the compound (III).

III. Preparation of the Compound (I)

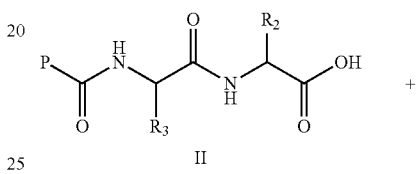

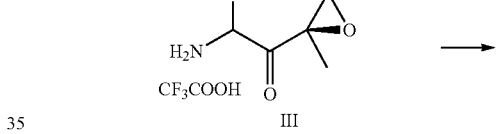

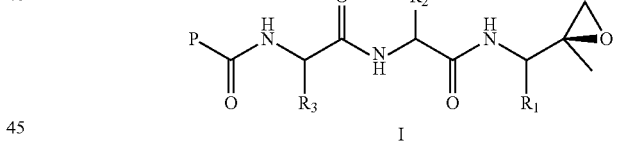

Preparation of the Compound (I):

The compound (II) and HOBt are dissolved in anhydrous DCM and the reaction solution is stirred at −5° C. for 10 min. EDI·HCl is added at the temperature and the reaction solution is stirred for 15-20 min. The compound (III) is added and the reaction solution is stirred for 15-20 min. DIPEA is added and the reaction solution is stirred for 20 min. The reaction solution is moved to room temperature for reaction. After the reaction is complete, the reaction solution is poured into water and extracted with DCM. The organic phases are combined and washed with dilute HCl, a NaHCO$_3$ solution and saturated brine respectively, and dried with anhydrous sodium sulfate. The solvent is evaporated to obtain the compound (I).

The preparation process of the compound of the present invention is described with the synthesis of specific compounds as follows:

I. Preparation of Acid Fragments:

The preparation of N-2,5-dichlorophenyl-2-formyl-O-methyl-L-serine-S-methyl-L-cysteine is taken as an example:

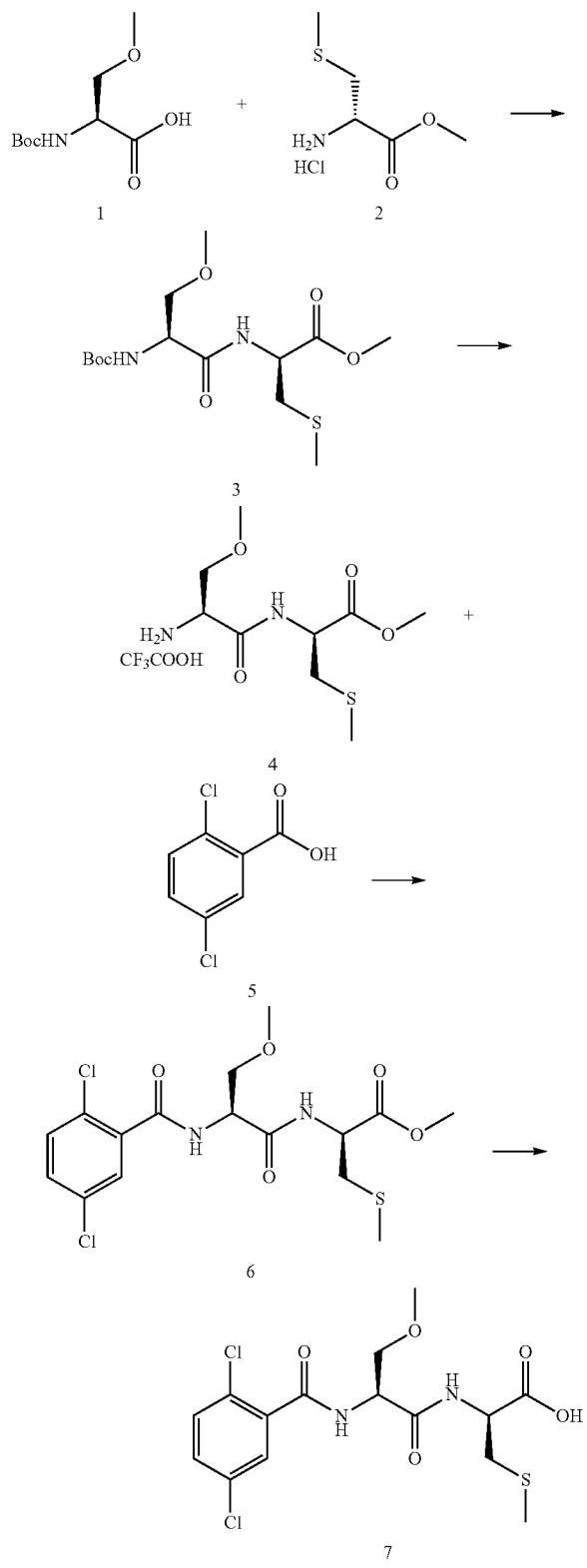

The compound 1 (1 g, 4.56 mmol) and HOBt (0.92 g, 6.84 mmol) are dissolved in anhydrous DCM (50 mL) and the reaction solution is stirred at −5° C. for 10 min. EDI·HCl (1.31 g, 6.84 mmol) is added at the temperature and the reaction solution is stirred for 15-20 min. The compound 2 (0.85 g, 4.56 mmol) is added and the reaction solution is stirred for 15-20 min. DIPEA (2.26 mL, 13.68 mmol) is added and the reaction solution is stirred for 20 min. The reaction solution is moved to room temperature for reaction. After the reaction is complete, the reaction solution is poured into ice water and extracted with DCM. The organic phases are combined and washed with 0.4 N HCl, 5% $NaHCO_3$ and saturated brine respectively, and dried with anhydrous sodium sulfate. The solvent is evaporated to obtain the compound 3.

The compound 3 (1 g, 2.85 mmol) is dissolved in anhydrous DCM (30 mL). TFA (5.13 mL) is added dropwise slowly at −5° C. After stirring for 0.5 h, the temperature is raised to room temperature and the reaction solution is stirred for 3 h. After the reaction is complete, the reaction solution is concentrated to obtain brown-red oil. The brown-red oil is slowly added to methyl tert-butyl ether, and the reaction solution is vigorously stirred to obtain a white solid. The white solid is filtered to obtain the compound 4.

The compound 5 (1 g, 5.24 mmol) and HOBt (1.06 g, 7.86 mmol) are dissolved in anhydrous DCM (50 mL) and the reaction solution is stirred at −5° C. for 10 min. EDI·HCl (1.50 g, 7.86 mmol) is added at the temperature and the reaction solution is stirred for 15-20 min. The compound 4 (1.91 g, 5.24 mmol) is added and the reaction solution is stirred for 15-20 min. DIPEA (2.47 mL, 15.72 mmol) is added and the reaction solution is stirred for 20 min. The reaction solution is moved to room temperature for reaction. After the reaction is complete, the reaction solution is poured into ice water and extracted with DCM. The organic phases are combined and washed with 0.4 N HCl, 5% $NaHCO_3$ and saturated brine respectively, and dried with anhydrous sodium sulfate. The solvent is evaporated to obtain the compound 6.

The compound 6 (1 g, 2.36 mmol) is dissolved in MeOH/$H_2O$ (20 mL/5 mL). A LiOH·$H_2O$ (0.14 g, 3.31 mmol) in $H_2O$ (1 mL) solution is added dropwise at 0° C. and the reaction solution is stirred for 2 h. The temperature is raised to room temperature for reaction for a certain time. Water is added and the pH is adjusted to 6-7 with hydrochloric acid. The reaction solution is extracted with ethyl acetate. The organic phase is washed with saturated brine, and dried with anhydrous sodium sulfate. The solvent is evaporated to obtain the compound 7, yield 90%, m.p.: 42.3-43.7° C.; $^1$H NMR (400 MHz, CDCl3) δ 2.13 (s, 3H), 3.02 (d, J=4.8 Hz, 2H), 3.43 (s, 3H), 3.61 (dd, J=17.2, 9.9 Hz, 2H), 3.93 (d, J=9.0 Hz, 2H), 4.89-4.78 (m, 2H), 7.35 (s, 2H), 7.41 (d, J=4.5 Hz, 1H), 7.44 (d, J=8.7 Hz, 1H), 7.58 (d, J=7.5 Hz, 1H), 7.64 (d, J=4.2 Hz, 1H); MS (ESI) m/z: 410.2 [M+H]$^+$.

The synthetic methods of all acid fragment compounds in the present invention are similar to that of 7.

The specific compounds synthesized and names thereof are as follows.

| No. | Structure | Chemical name and analysis data |
|---|---|---|
| 8 | 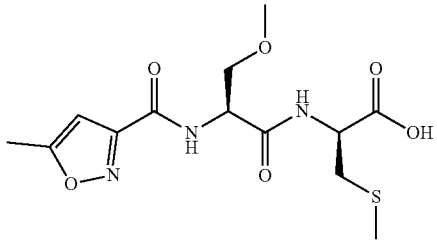 [SMILES: COC[C@H](NC(=O)c1cc(C)on1)C(=O)N[C@H](CSC)C(=O)O] | N-5-methylisoxazolyl-3-formyl-O-methyl-L-seryl-S-methyl-L-cysteine<br>Yield 90%, m.p.: 50.2-51.8° C.; $^1$H NMR (400 MHz, CDCl$_3$) δ 2.13 (s, 3H), 2.49 (s, J = 4.9 Hz, 3H), 3.07 – 2.91 (m, 2H), 3.40 (s, 3H), 3.67 – 3.56 (m, J = 8.8, 6.7 Hz, 1H), 3.88 (dd, J = 9.3, 4.2 Hz, 1H), 4.94 – 4.77 (m, 2H), 6.44 (s, 1H), 7.38 (s, J = 7.3, 3.5 Hz, 1H),7.50 (s, J = 11.4 Hz, 1H), 7.76 (s, J = 15.7, 7.5 Hz, 1H); MS (ESI) m/z: 346.1 [M + H]$^+$. |
| 9 | 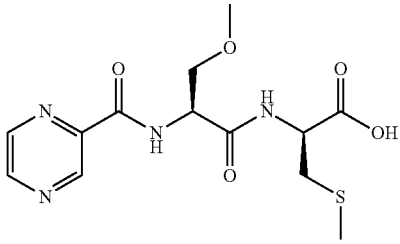 [SMILES: COC[C@H](NC(=O)c1cnccn1)C(=O)N[C@H](CSC)C(=O)O] | N-pyrazinyl-2-formyl-O-methyl-L-seryl-S-methyl-L-cysteine<br>Yield 90%, m.p.: 80.5-82.1° C.; $^1$H NMR (400 MHz, CDCl$_3$) δ 2.04 (s, 3H), 3.15 – 2.95 (m, 2H), 3.43 (s, 3H), 3.72 – 3.58 (m, 1H), 3.96 – 3.89 (m, J = 9.4, 7.4, 4.4 Hz, 1H), 4.98 – 4.81 (m, 2H), 7.43 (s, 1H), 7.55 (s, J = 7.5 Hz, 1H), 8.60 (s, 1H), 8.69 – 8.59 (m, 1H), 8.78 (s, J = 1.6 Hz, 1H), 9.37 (s, J = 4.0 Hz, 1H); MS (ESI) m/z: 343.1 [M + H]$^+$. |
| 10 | 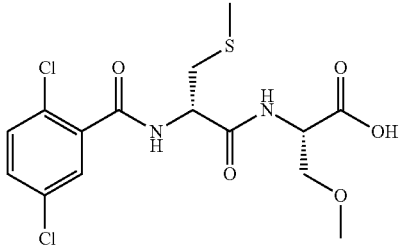 [SMILES: COC[C@H](NC(=O)[C@@H](CSC)NC(=O)c1cc(Cl)ccc1Cl)C(=O)O] | N-2,5-dichlorophenyl-2-formyl-S-methyl-L-cysteinyl-O-methyl-L-serine<br>Yield 90%, m.p.: 42.3-43.7° C.; $^1$H NMR (400 MHz, DMSO) δ 2.10 (dd, J = 14.3, 2.3 Hz, 3H), 2.49 – 2.41 (m, 3H), 2.96 – 2.77 (m, 2H), 3.24 (s, 1H), 3.53 (dd, J = 8.4, 3.8 Hz, 1H), 3.67 (dd, J = 9.4, 4.3 Hz, 1H), 4.43 (dt, J = 8.3, 4.5 Hz, 0H), 4.85 – 4.69 (m, 1H), 6.67 – 6.53 (m, 1H), 8.71 – 8.36 (m, 2H); MS (ESI) m/z: 410.2 [M + H]$^+$. |
| 11 | 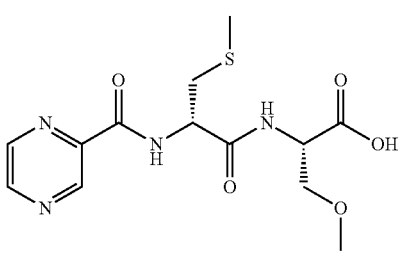 [SMILES: COC[C@H](NC(=O)[C@@H](CSC)NC(=O)c1cnccn1)C(=O)O] | N-pyrazinyl-2-formyl-S-methyl-L-cysteinyl-O-methyl-L-serine<br>Yield 90%, m.p.: 80.5-82.1° C.; $^1$H NMR (400 MHz, DMSO) δ 2.04 (d, J = 30.8 Hz, 3H), 2.93 (2, 2H), 3.25 (d, J = 2.0 Hz, 3H), 3.52 (dd, J = 6.7, 2.7 Hz, 1H), 3.71 – 3.66 (m, 1H), 4.46 (d, J = 3.6 Hz, 1H), 4.95 – 4.81 (m, 1H), 8.64 (dt, J = 27.7, 13.8 Hz, 1H), 8.84 – 8.74 (m, 2H), 8.91 (d, J = 2.3 Hz, 1H), 9.21 (s, 1H), 12.57 (s, 1H); MS (ESI) m/z: 343.1 [M + H]$^+$. |
| 12 | 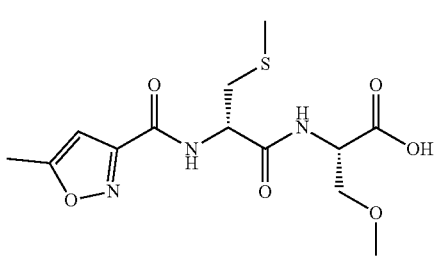 [SMILES: COC[C@H](NC(=O)[C@@H](CSC)NC(=O)c1cc(C)on1)C(=O)O] | N-5-methylisoxazolyl-3-formyl-S-methyl-L-cysteinyl-O-methyl-L-serine<br>Yield 90%, m.p.: 50.2-51.8° C.; $^1$H NMR (400 MHz, DMSO) δ 2.10 (dd, J = 14.3, 2.3 Hz, 3H), 2.49 – 2.41 (m, 3H), 2.96 – 2.77 (m, 2H), 3.24 (s, 1H), 3.53 (dd, J = 8.4, 3.8 Hz, 1H), 3.67 (dd, J = 9.4, 4.3 Hz, 1H), 4.43 (dt, J = 8.3, 4.5 Hz, 0H), 4.85 – 4.69 (m, 1H), 6.67 – 6.53 (m, 1H), 8.71 – 8.36 (m, 2H); MS (ESI) m/z: 346.1 [M + H]$^+$. |
| 13 | 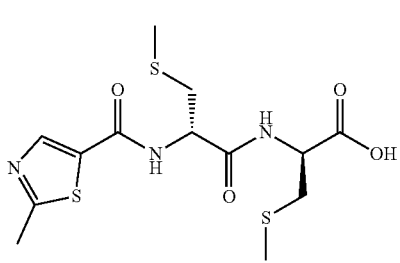 [SMILES: CSC[C@@H](NC(=O)[C@@H](CSC)NC(=O)c1cnc(C)s1)C(=O)O] | N-2-methylithiazolyl-5-formyl-S-methyl-L-cysteinyl-S-methyl-L-cysteine<br>Yield 90%, m.p.: 55.3-56.4° C.; $^1$H NMR (400 MHz, DMSO) δ 1.99 (s, J = 3.6, 1.8 Hz, 3H), 2.04 (s, 3H), 2.60 (s, 3H), 2.85 – 2.75 (m, 2H), 2.95 – 2.84 (m, 2H), 4.62 – 4.55 (m, 1H), 4.74 – 4.63 (m, 1H), 7.29 (s, J = 0.8 Hz, 1H), 7.58 (d, J = 7.5 Hz, 1H), 7.88 (d, J = 10.0 Hz, 1H), 8.08 (s, 1H); MS (ESI) m/z: 378.1 [M + H]$^+$. |

| No. | Structure | Chemical name and analysis data |
|---|---|---|
| 14 | 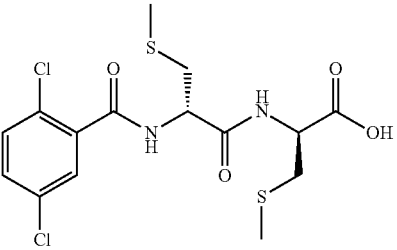 [SMILES: CSC[C@@H](NC(=O)[C@@H](CSC)NC(=O)c1cc(Cl)ccc1Cl)C(=O)O] | N-2,5-dichlorophenyl-2-formyl-S-methyl-L-cysteinyl-S-methyl-L-cysteine<br>Yield 90%, m.p.: 44.3-45.7° C.; $^1$H NMR (400 MHz, DMSO) δ 2.08 (s, 1H), 2.10 (s, 2H), 2.12 (s, 3H), 2.85 − 2.63 (m, 2H), 2.97 − 2.86 (m, 2H), 4.54 − 4.39 (m, J = 12.8, 7.9, 5.1 Hz, 1H), 4.80 − 4.65 (m, 1H), 7.51 (dt, J =4.0, 1.5 Hz, 1H), 7.55 (t, J = 1.4 Hz, 2H), 8.43 (d, J = 7.8 Hz, 1H), 8.52 (d, J = 8.2 Hz, 1H), 8.84 (d, J = 8.6 Hz, 1H); MS (ESI) m/z: 426.1 [M + H]$^+$. |
| 15 | 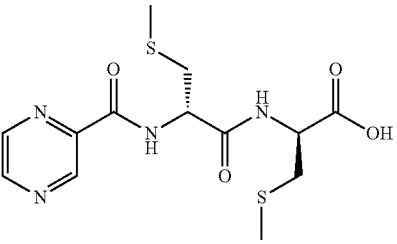 [SMILES: CSC[C@@H](NC(=O)[C@@H](CSC)NC(=O)c1cnccn1)C(=O)O] | N-pyrazinyl-2-formyl-S-methyl-L-cysteinyl-S-methyl-L-cysteine<br>Yield 90%, m.p.: 55.5-56.3° C.; $^1$H NMR (400 MHz, DMSO) δ 2.08 (dd, J = 7.2, 2.5 Hz, 6H), 2.81 − 2.68 (m, 1H), 3.01 − 2.83 (m, 3H), 4.50 − 4.40 (m, 1H), 4.92 − 4.77 (m, 1H), 8.63 (d, J = 7.9 Hz, 1H), 8.77 (d, J = 6.7 Hz, 1H), 8.82 (d, J = 8.9 Hz, 1H), 8.92 (d, J = 2.4 Hz, 1H), 9.21 (s, 1H); MS (ESI) m/z: 359.1 [M + H]$^+$. |
| 16 | 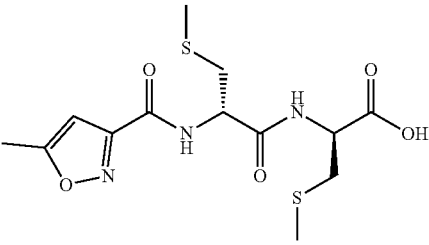 [SMILES: CSC[C@@H](NC(=O)[C@@H](CSC)NC(=O)c1cc(C)on1)C(=O)O] | N-5-methylisoxazolyl-3-formyl-S-methyl-L-cysteinyl-S-methyl-L-cysteine<br>Yield 90%, m.p.: 59.-60.2° C.; $^1$H NMR (400 MHz, DMSO) δ 2.07 (dd, J = 6.2, 2.3 Hz, 6H), 2.48 (s, J = 8.3 Hz, 3H), 2.82 − 2.71 (m, 1H), 2.96 − 2.82 (m, J = 13.5, 8.2, 4.2 Hz, 3H), 4.51 − 4.36 (m, 1H), 4.80 − 4.65 (m, 1H), 6.58 (s, J = 0.7 Hz, 1H), 8.50 (s, J = 7.8 Hz, 1H), 8.59 (s, J = 15.3, 5.4 Hz, 1H), 12.95 (s, 1H); MS (ESI) m/z: 362.1 [M + H]$^+$. |
| 17 | 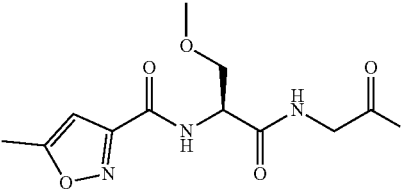 | N-5-methylisoxazolyl-3-formyl-O-methyl-L-seryl-glycine<br>Yield 90%, m.p.: 150-151° C.; $^1$H NMR (400 MHz, DMSO) 82.46 (d, J = 0.7 Hz, 3H), 3.26 (s, 3H), 3.52 (dd, J = 9.8, 3.9 Hz, 1H), 3.66 (dd, J = 9.8, 5.2 Hz, 1H), 4.14 (dd, J = 6.0, 3.6 Hz, 2H), 4.49 − 4.40 (m, 1H), 6.54 (s, J = 0.9 Hz, 1H), 8.30 (d, J = 8.0 Hz, 1H), 8.72 (t, J = 6.0 Hz, 1H); MS (ESI) m/z: 286.1 [M + H]$^+$. |
| 18 | 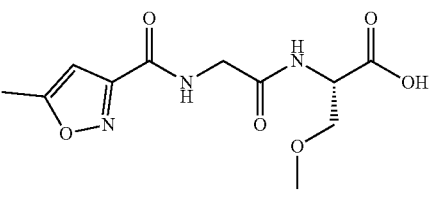 | N-5-methylisoxazolyl-3-formyl-glycyl-O-methyl-L-serine<br>Yield 90%, m.p.: 149.1-151.7° C.; $^1$H NMR (400 MHz, DMSO) δ 2.46 (d, J = 0.7 Hz, 3H), 3.26 (s, 3H), 3.52 (dd, J = 9.8, 3.9 Hz, 1H), 3.66 (dd, J = 9.8, 5.2 Hz, 1H), 3.92 (dd, J = 6.0, 3.6 Hz, 2H), 4.49 − 4.40 (m, 1H), 6.54 (s, J = 0.9 Hz, 1H), 8.30 (d, J = 8.0 Hz, 1H), 8.72 (t, J = 6.0 Hz, 1H); MS (ESI) m/z: 595.5 [M + H]$^+$. |
| 19 | 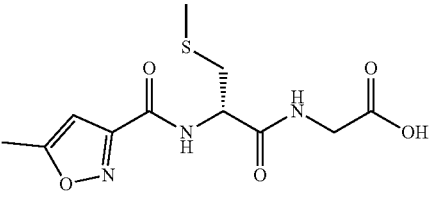 [SMILES: CSC[C@@H](NC(=O)c1cc(C)on1)C(=O)NCC(=O)O] | N-5-methylisoxazolyl-3-formyl-S-methyl-L-cysteinyl-glycine<br>Yield 90%, m.p.: 150.1-151.4° C.; $^1$H NMR (400 MHz, DMSO) δ 2.08 (s, 2H), 2.48 (s, 3H), 2.98 − 2.80 (m, J = 23.6, 13.8, 7.1 Hz, 2H), 3.78 (dd, J = 5.7, 3.4 Hz, 2H), 4.69 (td, J = 9.5, 4.4 Hz, 1H), 6.59 (s, J = 0.8 Hz, 1H), 8.49 (t, 1H), 8.65 (d, J = 8.6 Hz, 1H), 12.60 (s, 1H); MS (ESI) m/z: 302.1 [M + H]$^+$. |

| No. | Structure | Chemical name and analysis data |
|---|---|---|
| 20 | 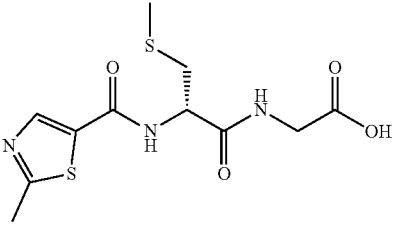 [SMILES: CSC[C@@H](NC(=O)c1cnc(C)s1)C(=O)NCC(=O)O] | N-2-methylthiazolyl-5-formyl-S-methyl-L-cysteinyl-glycine<br>Yield 90%, m.p.: 129.4-131.6° C.; $^1$H NMR (400 MHz, CD$_3$OD_SPE) 82.14 (s, J = 7.8 Hz, 3H), 2.72 (s, 3H), 2.91 – 2.80 (m, J = 14.0, 7.3 Hz, 1H), 3.14-3.00 (m, 1H), 3.96 (d, J = 13.6, 5.5 Hz, 2H), 4.81 – 4.72 (m, J = 9.7, 4.9 Hz, 1H), 8.23 (s, 1H); MS (ESI) m/z: 318.1 [M + H]$^+$. |

II. Preparation of Amine Fragments:

The preparation of compound (S)-2-amino-4-methyl-1-((R)-2-methyloxirane-2-yl)pentan-1-one 2,2,2-trifluoroacetate (28) is taken as an example:

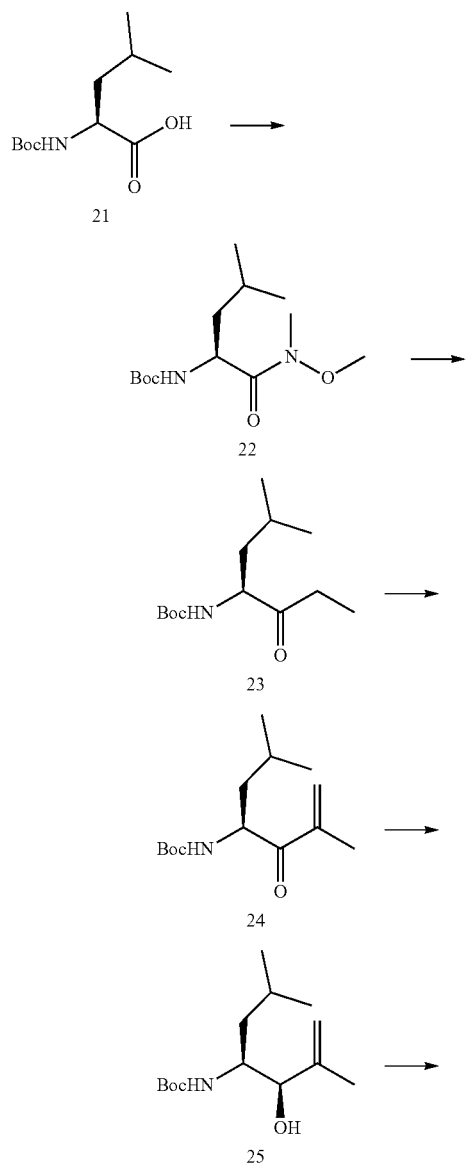

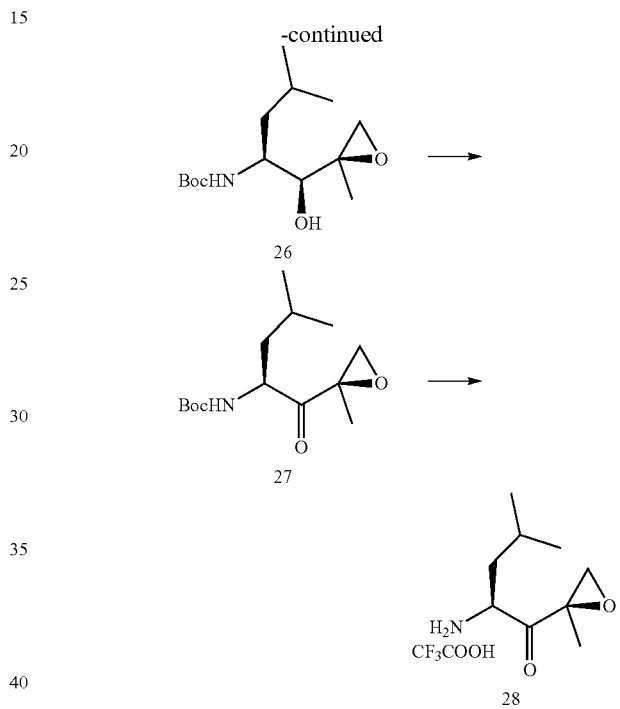

The compound 21 (10.0 g, 43.23 mmol) and HOBt (5.8 g, 43.23 mmol) are dissolved in DCM (100 mL). EDC·HCl (11.65 g, 64.85 mmol) is added. After stirring at −5° C. for 15 min, dimethylhydroxylamine hydrochloride (4.21 g, 43.23 mmol) is added. DIPEA (13.97 g, 108.08 mmol) is added after 15 min. Reaction is performed at low temperature for 25 min. After the reaction is complete at room temperature, the reaction solution is extracted with DCM. The organic phase is washed with 1N HCl, 5% NaHCO$_3$ and saturated brine, and dried with anhydrous sodium sulfate. The solvent is evaporated to obtain the compound 22.

N-tert-butoxycarbonyl-L-leucine-N'-methoxyl-N'-formamide 22 (0.5 mol) is weighed, added into a reaction flask and dissolved with 500 mL of tetrahydrofuran. At −20° C., ethyl magnesium bromide (2.0 M, 750 mL) is added dropwise. After dropwise adding, the temperature is raised to room temperature for reaction overnight. 1N HCl is added dropwise slowly to quench the reaction. Extraction is performed with ethyl acetate. The extract is washed with saturated brine. The organic phase is dried and concentrated to obtain the compound 23.

The compound 23 (0.4 mol) is weighed and dissolved with 400 mL tetrahydrofuran. Piperidine acetate (1.5 mol), piperidine (1.0 mol) and paraformaldehyde (2.0 mol) are added. After refluxing for 3 h, paraformaldehyde (2.0 mol) is added. The reaction is tested by TLC to completion. An appropriate amount of water is added and extraction is performed with ethyl acetate. The extract is washed with 1N HCl and saturated brine 1 time respectively. The organic phase is dried and concentrated to obtain the compound 24.

Aluminum isopropoxide (0.3 mol) and isopropanol (3 mol) are weighed, added to 200 mL of toluene and the compound 24 (0.3 mol), dissolved with 100 mL of toluene, and added dropwise to the reaction system at room temperature. After dropwise adding, the reaction is performed at 50° C., and tested by TLC to completion. An appropriate amount of water is added and then extraction is performed with ethyl acetate. The extract is washed with 1N HCl and saturated brine 1 time respectively. The organic phase is dried and concentrated to obtain the compound 25.

The compound 25 (0.2 mol) is weighed and dissolved in 200 mL of dichloromethane. Then vanadium acetylacetonate (0.04 mol) is added. Under nitrogen protection, the reaction solution is cooled to 0° C. in an ice bath. Tert-Butyl hydroperoxide is added dropwise slowly. The reaction solution is stirred more vigorously overnight, and tested by TLC that the raw materials disappear. An appropriate amount of water is added and extraction is performed with dichloromethane. The extract is washed with saturated sodium thiosulfate and saturated brine respectively. The organic phase is dried, concentrated and purified to obtain the compound 26.

The compound 26 (0.12 mol) is dissolved in 100 mL of dimethyl sulfoxide. Diisopropylethylamine (0.24 mol) is added. Pyridine sulfur trioxide (0.24 mol) is added in batches in an ice bath. The temperature is raised to room temperature for reaction. After the reaction is complete tested by TLC, an appropriate amount of water is added and extraction is performed with ethyl acetate. The extract is washed with 1N HCl and saturated brine. The organic phase is dried and concentrated to obtain the compound 27.

The compound 27 (1.0 g, 3.69 mmol) is dissolved in anhydrous DCM (10 mL). TFA (3 mL) is added dropwise slowly at −5° C. After stirring for 0.5 h, the temperature is raised to room temperature and the reaction solution is stirred for 3 h and then tested. After the reaction is complete, the reaction solution is concentrated to obtain brown-red oil. The brown-red oil is slowly added to methyl tert-butyl ether, and the reaction solution is vigorously stirred to obtain a white solid. The white solid is filtered to obtain the compound 28. The yield is 85%, m.p.: 83-84° C. 1H NMR (400 MHz, CDCl3): δ 0.97 (—CH3, d, J=6.4 Hz, 3H), 1.28 (—CH3, d, J=14.1 Hz, 3H), 1.83-1.64 (—CH, m, 1H), 1.92-1.84 (—CH2, m, 2H), 2.93 ((—CH, d, J=4.5 Hz, 1H), 3.16 (—CH, d, J=4.5 Hz, 1H), 4.05 (—CH, dd, J=9.7, 3.1 Hz, 1H); MS (ESI) m/z: 172.1 [M+H]⁺.

The synthetic method of the compound 29 in the present invention is similar to that of the compound 28.

The specific compounds synthesized and names thereof are as follows.

| No. | Structure | Chemical name and analysis data |
|---|---|---|
| 29 | (structure with phenyl, NH2, ketone, methyloxirane, CF3COOH) | (S)-2-amino-1-((R)-2-methyloxirane-2-yl)-3-phenylpropan-1-one 2,2,2-trifluoroacetate Yield 76%, m.p.: 118-119° C.; ¹H NMR (400 MHz, CDCl₃): δ 1.55 (—CH₃, s, 3H), 2.99 (—CH, d, J = 4.4 Hz, 1H), 3.05 (—CH, dd, J = 14.3, 7.9 Hz, 1H), 3.24 (—CH, d, J = 4.4 Hz, 1H), 3.37 (—CH, dd, J = 14.3, 4.4 Hz, 1H), 4.29 (—CH, dd, J = 7.8, 4.6 Hz, 1H), 7.38-7.21 (—Ph, m, 5H); MS (ESI) m/z: 206.3 [M + H]⁺. |

III. Preparation of Compound of Formula (I)

The preparation of 2,5-dichlorobenzoyl-L-methylserine-S-methyl-L-cysteinyl-methyloxirane (30) is taken as an example:

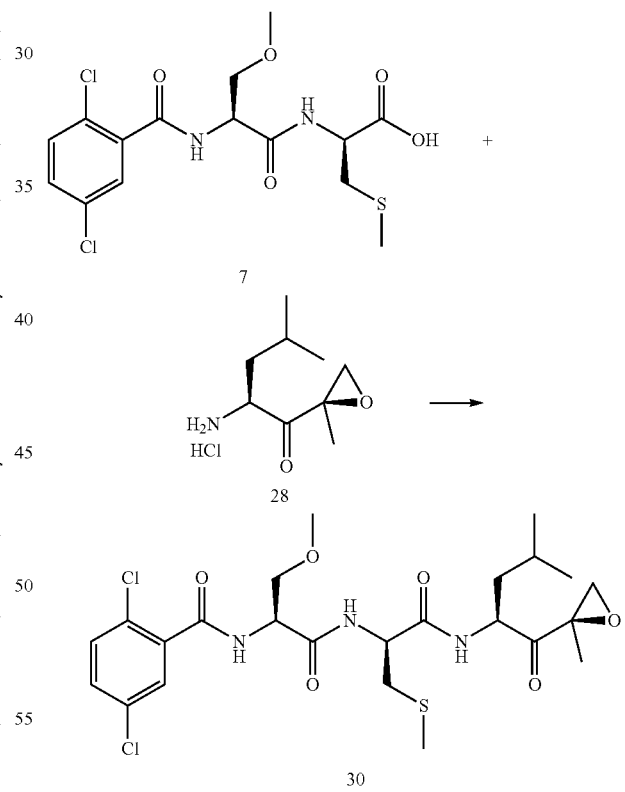

The compound 7 (1 g, 2.4 mmol) and HOBt (0.5 g, 3.6 mmol) are dissolved in DCM. EDC·HCl (0.7 g, 3.6 mmol) is added. After stirring at −5° C. for 15 min, the compound 28 (0.7 g, 2.4 mmol) is added. DIPEA (1.2 mL, 7.2 mmol) is added after 15 min. Reaction is performed at low temperature for 25 min. After the reaction is complete at room temperature, the reaction solution is extracted with DCM. The organic phase is washed with 1N HCl, 5% NaHCO₃ and saturated brine, and dried with anhydrous sodium sulfate. The solvent is evaporated to obtain the compound 30. The yield is 60%, m.p.: 60.8-62.3° C.; 1H NMR (400 MHz, CDCl$_3$) δ 0.97-0.84 (m, 6H), 1.35-1.23 (m, 2H), 1.52-1.47 (m, 3H), 1.70-1.58 (m, 1H), 2.18-2.06 (m, 3H), 2.84-2.72 (m, 1H), 2.87 (dt, J=10.4, 5.2 Hz, 1H), 3.09-2.93 (m, 1H), 3.31-3.25 (m, 1H), 3.49-3.38 (m, 3H), 3.71-3.55 (m, 1H), 4.04-3.87 (m, 1H), 4.69-4.50 (m, 2H), 4.85-4.71 (m, 1H), 7.18 (dd, J=11.0, 4.7 Hz, 1H), 7.76-7.63 (m, 1H), 7.40-7.32 (m, 2H); $^{13}$C NMR (101 MHz, CDCl$_3$) δ15.94, 16.68, 21.17, 23.29, 25.15, 35.91, 39.87, 50.50, 52.08, 52.34, 53.57, 59.06, 59.32, 71.19, 129.04, 130.17, 131.45, 131.69, 133.31, 135.37, 165.24, 169.12, 169.95, 208.06; HRMS calcd for C$_{24}$H$_{33}$Cl$_2$N$_3$O$_6$SNa, [M+Na]$^+$584.1359, found 584.1303.

The synthetic methods of all compounds in the present invention are similar to that of the compound 30.

The specific compounds synthesized and names thereof are as follows.

| No. | Structure | Chemical name and analysis data |
|---|---|---|
| 31 | 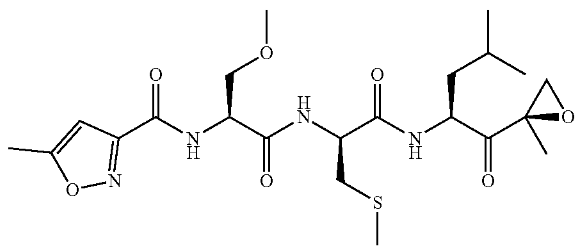 [SMILES: COC[C@H](NC(=O)c1cc(C)on1)C(=O)N[C@H](CSC)C(=O)N[C@@H](CC(C)C)C(=O)[C@@]1(C)CO1] | N-5-methylisoxazolyl-3-formyl-O-methyl-L-seryl-S-methyl-L-cysteinyl-L-leucyl-methyloxirane<br>Yield 78%, m.p.: 70.2-72.7° C.; $^1$H NMR (400 MHz, CDCl$_3$) δ 0.95-0.90 (m, 6H), 1.34-1.22 (m, 2H), 1.50 (s, J = 5.4 Hz, 3H), 1.71-1.58 (m, 1H), 2.10 (s, 3H), 2.47 (s, J = 0.8 Hz, 3H), 2.79 (ddd, J = 14.0, 10.6, 6.6 Hz, 1H), 2.87 (t, J = 6.1 Hz, 1H), 3.01-2.90 (m, 1H), 3.42 (s, 3H), 3.69-3.53 (m, 1H), 3.96-3.80 (m, 1H), 4.65 (s, 2H), 4.76-4.64 (m, 1H), 6.42 (s, 1H), 6.98 (s, J = 13.6, 6.6 Hz, 1H), 7.57 (s, 2H); $^{13}$C NMR (101 MHz, CDCl$_3$) δ 12.32, 15.87, 16.66, 21.23, 23.34, 25.13, 35.86, 39.92, 50.45, 52.04, 52.32, 52.76, 59.05, 59.29, 71.31, 101.28, 157.99, 159.42, 169.06, 169.99, 171.40, 208.05; HRMS calcd for C$_{22}$H$_{34}$N$_4$O$_7$SNa, [M + Na]$^+$ 521.2040, found 521.2226. |
| 32 | 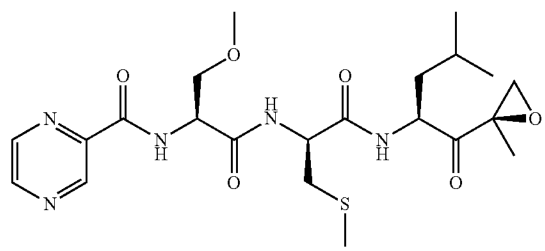 [SMILES: COC[C@H](NC(=O)c1cnccn1)C(=O)N[C@H](CSC)C(=O)N[C@@H](CC(C)C)C(=O)[C@@]1(C)CO1] | N-pyrazinyl-2-formyl-O-methyl-L-seryl-S-methyl-L-cysteinyl-L-leucyl-methyloxirane<br>Yield 80%, m.p.: 50-51° C.; $^1$H NMR (400 MHz, CDCl$_3$) δ 0.99-0.89 (m, 6H), 1.42-1.17 (m, 2H), 1.51-1.46 (m, 3H), 1.70-1.60 (m, 1H), 2.18-2.04 (m, 3H), 2.83-2.75 (m, 1H), 2.87 (dd, J = 6.5, 3.8 Hz, 1H), 3.03-2.92 (m, 1H), 3.35-3.21 (m, 1H), 3.51-3.40 (m, 3H), 3.74-3.59 (m, 1H), 4.01-3.86 (m, 1H), 4.66-4.51 (m, 2H), 4.76 (ddt, J = 12.4, 8.0, 3.1 Hz, 1H), 7.25-6.83 (m, 2H), 8.63-8.48 (m, 2H), 8.78 (s, J = 4.4, 2.1 Hz, 1H), 9.37 (s, J = 1.4 Hz, 1H); $^{13}$C NMR (101 MHz, CDCl$_3$) δ 15.88, 16.68, 21.19, 23.37, 25.17, 35.81, 39.87, 50.68, 51.91, 52.07, 52.77, 53.15, 59.31, 71.51, 142.79, 142.84, 144.32, 144.39, 163.41, 169.50, 170.01, 208.10; HRMS calcd for C$_{22}$H$_{33}$N$_5$O$_7$SNa, [M + Na]$^+$ 518.2043, found 518.2042. |
| 33 | 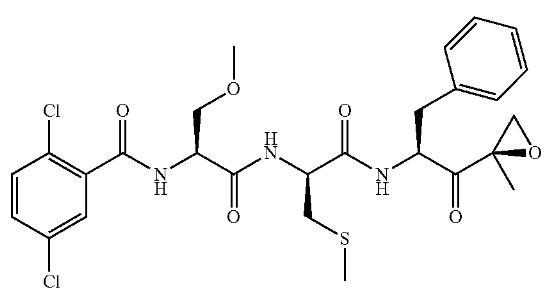 [SMILES: COC[C@H](NC(=O)c1cc(Cl)ccc1Cl)C(=O)N[C@H](CSC)C(=O)N[C@@H](Cc1ccccc1)C(=O)[C@@]1(C)CO1] | N-2,5-dichlorophenyl-2-formyl-O-methyl-L-seryl-S-methyl-L-cysteinyl-L-phenylalanyl-methyloxirane<br>Yield 78%, m.p.: 50.7-52.3° C.; $^1$H NMR (400 MHz, CDCl$_3$) 1.31-1.20 (m, 3H), 2.10-1.92 (m, 3H), 2.78-2.64 (m, 1H), 3.00-2.79 (m, 2H), δ 7.71-7.67 (m, 1H), 3.26-3.15 (m, 1H), 3.47-3.35 (m, 3H), 3.60 (dt, J = 9.3, 6.3 Hz, 1H), 3.98-3.90 (m, 1H), 4.62-4.49 (m, 1H), 7.41-7.33 (m, 2H), 4.77-4.67 (m, 1H), 5.47-5.33 (m, 1H), 7.25-7.16 (m, 5H), 7.28 (dd, J = 6.8, 1.4 Hz, 1H); $^{13}$C NMR (101 MHz, CDCl$_3$) δ 15.59, 16.58, 35.56, 37.03, 51.95, 52.47, 53.11, 53.68, 59.27, 59.33, 71.12, 127.09, 127.22, 129.10, 129.32, 129.38, 130.23, 130.41, 131.55,131.72, 136.91, 166.84, 169.57, 170.75, 210.53; HRMS calcd for C$_{27}$H$_{31}$Cl$_2$N$_3$O$_6$SNa, [M + Na]$^+$ 618.1202, found 618.1202. |
| 34 | 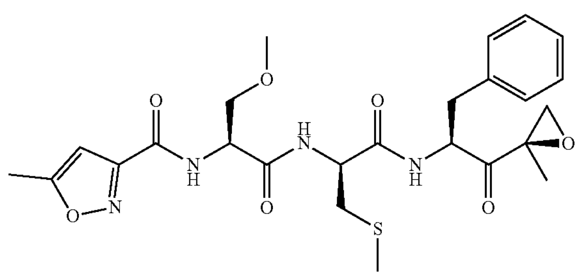 | N-5-methylisoxazolyl-3-formyl-O-methyl-L-seryl-S-methyl-L-cysteinyl-L-phenylalanyl-methyloxirane<br>Yield 75%, oily liquid; $^1$H NMR (400 MHz, CDCl$_3$) δ 1.27 (s, J = 11.7 Hz, 3H), 2.02 (s, 3H), 2.49 (s, J = 3.9 Hz, 3H), 2.83-2.62 (m, 2H), 2.96-2.83 (m, 2H), 3.22-3.07 (m, 1H), 3.30 (t, J = 4.8 Hz, 1H), 3.41 (s, J = 7.6, 3.9 Hz, 3H), 3.61-3.52 (m, 1H), 3.95-3.79 (m, 1H), 4.51 (dd, J = 12.7, 6.8 Hz, 1H), 4.73-4.62 (m, 1H), 4.82 (dd, J = 13.1, 8.5 Hz, 1H), 6.43 (dd, J = 9.8, 4.8 Hz, 1H), 7.25-6.91 (m, 5H), 7.34-7.27 (m, 2H)7.58 (s, 1H); $^{13}$C NMR (101 MHz, CDCl$_3$) δ 12.27, 15.15, 16.42, 36.70, 37.12, 51.64, 52.39, 53.08, 54.08, 58.98, 59.57, 71.34, 100.03, 125.09, 127.19, 128.59, 128.66, 129.35, 136.40, 150.40, 160.48, 169.20, 169.54, 170.17, 210.53; HRMS calcd for C44H57N5O7Na, [M + Na]$^+$ 790.4150, found 790.4139. |

| No. | Structure | Chemical name and analysis data |
|---|---|---|
| 35 | 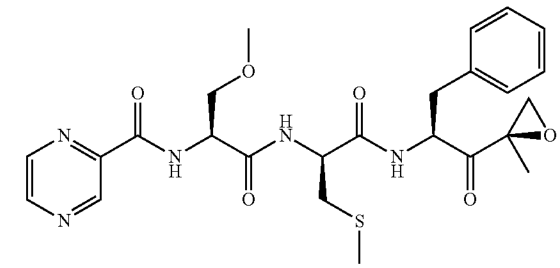 [SMILES: COC[C@H](NC(=O)c1cnccn1)C(=O)N[C@H](CSC)C(=O)N[C@@H](Cc1ccccc1)C(=O)[C@@]1(C)CO1] | N-pyrazinyl-2-formyl-O-methyl-L-seryl-S-methyl-L-cysteinyl-L-phenylalanyl-methyloxirane<br>Yield 50%, m.p.: 46.1-47.6° C.; $^1$H NMR (400 MHz, CDCl$_3$) 1.25 (s, 3H), 2.10-1.92 (m, 3H), 2.78-2.64 (m, 1H), 3.05-2.80 (m, 2H), 3.32-3.13 (m, 1H), 3.50-3.42 (m, 3H), 3.68-3.58 (m, 1H), 3.99-3.88 (m, 1H), 4.62-4.46 (m, 1H), 4.78-4.65 (m, 1H), 5.49-5.27 (m, 1H), 7.15-7.06 (m, 1H), 7.24-7.16 (m, 3H), 7.37-7.28 (m, 1H), 8.69-8.43 (m, 2H), 8.86-8.73 (m, 1H), δ 9.52-9.29 (m, 1H); $^{13}$C NMR (101 MHz, CDCl$_3$) δ 15.55, 16.54, 36.92, 37.29, 51.22, 51.94, 53.10, 54.51, 59.28,<br>59.38, 71.49, 125.53, 127.16, 127.46, 128.64, 129.33, 136.92, 142.78, 144.34, 145.12, 147.52, 161.68, 169.55, 171.14, 210.53; HRMS calcd for C25H31N5O6SNa, [M + Na]+ 552.1887, found 552.1889. |
| 36 | 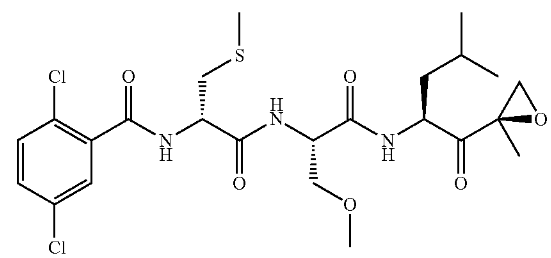 [SMILES: COC[C@H](NC(=O)[C@@H](CSC)NC(=O)c1cc(Cl)ccc1Cl)C(=O)N[C@@H](CC(C)C)C(=O)[C@@]1(C)CO1] | N-2,5-dichlorophenyl-2-formyl-S-methyl-L-cysteinyl-O-methyl-L-seryl-L-leucyl-methyloxirane<br>Yield 78%, m.p.: 59.8-60.3° C.; $^1$H NMR (400 MHz, CDCl$_3$) 0.93-0.84 (m, 6H), 1.25 (t, J = 3.5 Hz, 3H), 1.37 (d, J = 4.7 Hz, 2H), 1.57-1.54 (m, 1H), 2.25-2.15 (m, 3H), 2.66-2.51 (m, 1H), 2.87 (dd, J = 14.1, 10.6 Hz, 1H), 2.98 (dd, J = 13.0, 3.9 Hz, 1H), 3.42 (d, J = 12.5 Hz, 3H), 3.40-3.32 (m, 1H), 3.60-3.55 (m, 1H), 3.92-3.85 (m, 1H), 4.54 (ddd, J = 12.2, 10.6, 4.3 Hz, 1H), 5.06 (dddd, J = 27.6, 19.7, 13.7, 10.3 Hz, 2H), 7.34 (ddd, J = 3.1, 2.4, 1.8 Hz, 3H), 7.47 (dd, J = 2.1, 0.6 Hz, 1H), 7.69 (s, J =<br>2.2, 1.1 Hz, 1H), δ 7.93 (s, J = 21.3, 2.5 Hz, 1H), 13C NMR (101 MHz, CDCl3) δ, 15.52, 15.67, 22.70, 22.82, 29.68, 35.47, 36.92, 51.10, 51.90, 53.65, 53.87, 53.90, 59.38, 71.13, 127.08, 128.60, 129.39, 130.17, 131.49, 131.82, 165.54, 169.33, 170.10, 210.35; HRMS calcd for C$_{24}$H$_{33}$Cl$_2$N$_3$O$_6$SNa, [M + Na] 584.1359, found 584.1303. |
| 37 | 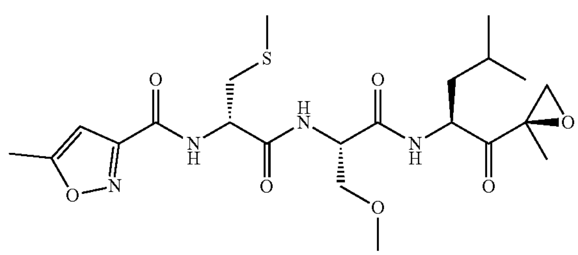 [SMILES: COC[C@H](NC(=O)[C@@H](CSC)NC(=O)c1cc(C)on1)C(=O)N[C@@H](CC(C)C)C(=O)[C@@]1(C)CO1] | N-5-methylisoxazolyl-3-formyl-S-methyl-L-cysteinyl-O-methyl-L-seryl-L-leucyl-methyloxirane<br>Yield 80%, m.p.: 49.5-51.8° C.; $^1$H NMR (400 MHz, CDCl$_3$) δ 0.83 (s, 6H), 1.25 (s, 3H), 1.32 (d, J = 7.4 Hz, 1H), 1.50 (d, J = 6.2 Hz, 2H), 2.22 (s, 3H), 2.48 (s, 3H), 2.93 (dd, J = 34.2, 11.1 Hz, 3H), 3.32 (dd, J = 17.3, 9.0 Hz, 2H), 3.42 (s, J = 9.7 Hz, 2H), 3.83 (s, 1H), 4.77-4.47 (m, 3H), 6.41 (s, 1H), 7.11-6.92 (m, 2H) 7.62 (s, 1H); $^{13}$C NMR (101 MHz, CDCl$_3$) δ 12.35, 15.59, 16.42, 22.62, 22.80, 29.67, 35.43, 36.99, 51.12, 51.86, 53.08, 53.66, 53.86, 59.35, 71.40, 101.34, 169.30, 169.52, 170.00,<br>170.10, 171.58, 210.82; HRMS calcd for C$_{22}$H$_{34}$N$_4$O$_7$SNa, [M + Na]$^+$ 521.2040, found 521.2037. |
| 38 | 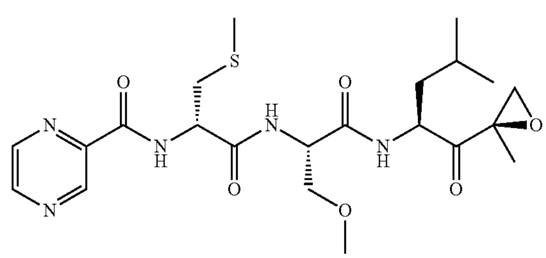 [SMILES: COC[C@H](NC(=O)[C@@H](CSC)NC(=O)c1cnccn1)C(=O)N[C@@H](CC(C)C)C(=O)[C@@]1(C)CO1] | N-pyrazinyl-2-formyl-S-methyl-L-cysteinyl-O-methyl-L-seryl-L-leucyl-methyloxirane<br>Yield 50%, m.p.: 59.6-61.2° C.; $^1$H NMR (400 MHz, CDCl3) 0.96-0.93 (m, 6H), 1.26 (dd, J = 13.3, 4.0 Hz, 2H), 1.33 (d, J = 4.7 Hz, 3H), 1.64-1.56 (m, 3H), 2.23-2.18 (m, 3H), 3.08-2.95 (m, 2H), 3.40 (d, J = 5.6 Hz, 3H), 3.49-3.47 (m, 1H), 3.86-3.80 (m, 1H), 4.67-4.51 (m, 2H), 5.15 (td, J = 9.3, 4.6 Hz, 1H), 7.16 (dd, J = 44.1, 7.9 Hz, 2H), 8.62-8.49 (m, 2H), 8.83-8.76 (m, 1H), δ 9.40 (dd, J = 8.0, 5.2 Hz, 1H); $^{13}$C NMR (101 MHz, CDCl$_3$) δ 15.60, 15.73, 22.62, 22.80, 22.90, 29.68, 37.03,<br>51.23, 51.76, 53.00, 53.49, 53.59, 59.36, 71.48, 142.84, 143.69, 144.37, 147.85, 163.82, 169.67, 170.00, 210.93; HRMS calcd for C22H33N5O6SNa, [M + Na]$^+$ 518.2043, found 518.2041. |

| No. | Structure | Chemical name and analysis data |
|---|---|---|
| 39 | 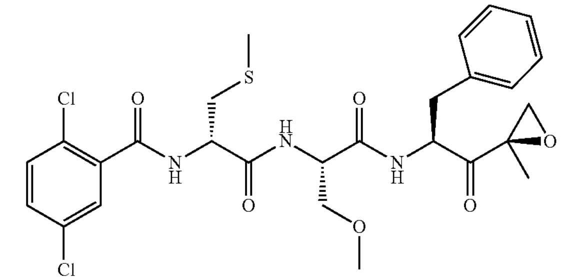 [SMILES: COC[C@H](NC(=O)[C@@H](CSC)NC(=O)c1cc(Cl)ccc1Cl)C(=O)N[C@@H](Cc1ccccc1)C(=O)[C@@]1(C)CO1] | N-2,5-dichlorophenyl-2-formyl-S-methyl-L-cysteinyl-O-methyl-L-seryl-L-phenylalanyl-methyloxirane<br>Yield 80%, m.p.: 51.2-52.7 °C.; $^1$H NMR (400 MHz, CDCl$_3$) 2.16 (d, J = 2.9 Hz, 3H), 2.51-2.43 (m, 3H), 2.93 (ddd, J = 23.3, 12.0, 7.8 Hz, 3H), 3.21-3.14 (m, 1H), 3.29-3.23 (m, 3H), 3.56-3.44 (m, 1H), 3.84 (dt, J = 17.3, 8.6 Hz, 1H), 4.61 (ddt, J = 40.1, 33.3, 14.0 Hz, 3H), 6.44 (dd, J = 18.4, 3.1 Hz, 1H), 7.22-7.12 (m, 4H), δ 7.37 (dd, J = 16.0, 5.2 Hz, 1H); $^{13}$C NMR (101 MHz, CDCl$_3$) δ 14.09, 15.71, 35.58, 36.83, 51.09, 52.83, 53.40, 53.67, 59.04, 59.09, 71.19, 127.00, 127.04, 128.57, 129.40,<br><br>129.44, 129.46, 129.50, 131.46, 131.54, 131.82, 133.35, 136.03, 165.50, 169.66, 169.95, 210.59; HRMS calcd for C$_{27}$H$_{31}$Cl$_2$N$_3$O$_6$SNa, [M + Na]$^+$ 618.1202, found 618.1202. |
| 40 | 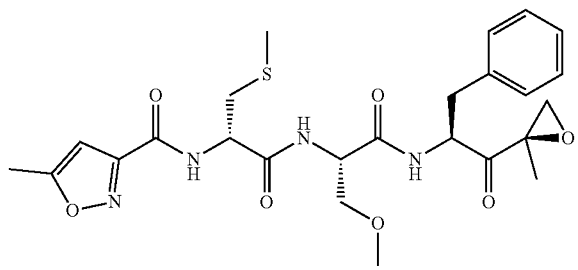 [SMILES: COC[C@H](NC(=O)[C@@H](CSC)NC(=O)c1cc(C)on1)C(=O)N[C@@H](Cc1ccccc1)C(=O)[C@@]1(C)CO1] | N-5-methylisoxazolyl-3-formyl-S-methyl-L-cysteinyl-O-methyl-L-seryl-L-phenylalanyl-methyloxirane<br>Yield 80%, oily liquid; $^1$H NMR (400 MHz, CDCl$_3$) 1.25 (s, 3H), 2.25-2.18 (m, 3H), 3.07-2.90 (m, 3H), 3.23-3.14 (m, 1H), 3.27 (dt, J = 11.6, 3.9 Hz, 3H), 3.43-3.34 (m, 1H), 3.83 (dd, J = 8.3, 3.2 Hz, 1H), 4.82-4.45 (m, 3H), 7.25-7.18 (m, 3H), 7.44-7.27 (m, 2H), 8.59 (dd, J = 3.6, 2.2 Hz, 1H), 8.83-8.78 (m, 1H), δ 9.45-9.35 (m, 1H); $^{13}$C NMR (101 MHz, CDCl$_3$) 812.02, 15.66, 15.90, 36.86, 52.47, 52.90, 53.20, 53.60, 59.06, 59.11, 71.23, 100.38, 127.02, 128.57, 128.62, 129.45, 129.53, 136.04,<br><br>150.26, 161.66, 169.70, 169.74, 170.03, 210.52; HRMS calcd for C$_{25}$H$_{32}$N$_4$O$_7$SNa, [M + Na]$^+$ 555.1883, found 555.1881. |
| 41 | 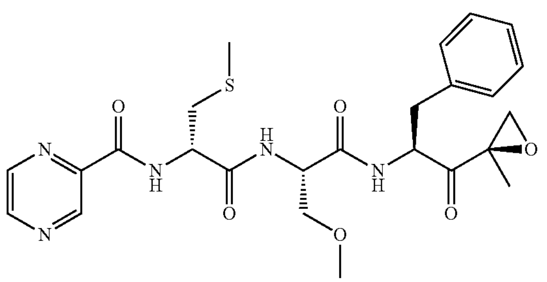 [SMILES: COC[C@H](NC(=O)[C@@H](CSC)NC(=O)c1cnccn1)C(=O)N[C@@H](Cc1ccccc1)C(=O)[C@@]1(C)CO1] | N-pyrazinyl-2-formyl-S-methyl-L-cysteinyl-O-methyl-L-seryl-L-phenylalanyl-methyloxirane<br>Yield 50%, m.p.: 49.7-51.2° C.; $^1$H NMR (400 MHz, CDCl$_3$) 1.25 (s, 3H), 2.23-2.17 (m, 3H), 3.02-2.90 (m, 3H), 3.22-3.16 (m, 1H), 3.31-3.26 (m, 3H), 3.41 (ddd, J = 11.1, 7.3, 4.3 Hz, 1H), 3.77 (td, J = 9.0, 4.1 Hz, 2H), 4.80-4.46 (m, 3H), 7.16 (ddd, J = 23.3, 14.7, 6.8 Hz, 5H), 8 7.42-7.33 (m, 3H); $^{13}$C NMR (101 MHz, CDCl$_3$) δ 14.10, 15.83, 35.54, 36.86, 52.47, 52.77, 52.90, 53.20, 59.06, 59.11, 71.23, 127.02, 128.57, 128.59, 129.42, 129.45, 136.07, 142.85, 144.38, 147.84, 169.61, 169.74,<br><br>169.95, 210.35; HRMS calcd for C$_{25}$H$_{31}$N$_5$O$_6$SNa, [M + Na]$^+$ 552.1887, found 552.1888. |
| 42 | 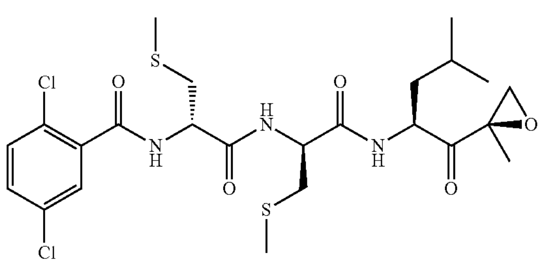 [SMILES: CSC[C@@H](NC(=O)c1cc(Cl)ccc1Cl)C(=O)N[C@H](CSC)C(=O)N[C@@H](CC(C)C)C(=O)[C@@]1(C)CO1] | N-2,5-dichlorophenyl-2-formyl-S-methyl-L-cysteinyl-S-methyl-L-cysteinyl-L-leucyl-methyloxirane<br>Yield 78%, m.p.: 163.1-164.5° C.; $^1$H NMR (400 MHz, CDCl$_3$) δ 0.91 (dd, 6H), 1.23 (s, J = 11.3 Hz, 3H), 1.60-1.52 (m, 1H), 1.75-1.64 (m, 2H), 2.14 (d, 3H), 2.22 (d, 3H), 2.91-2.74 (m, 2H), 3.14-2.92 (m, 3H), 3.35-3.27 (m, 1H), 4.66-4.52 (m, 2H), 4.83-4.68 (m, 1H), 6.99 (s, J = 18.3, 8.2 Hz, 1H), 7.24 (s, 1H), 7.28 (d, J = 7.5 Hz, 1H), 7.37-7.35 (m, 1H), 7.55-7.49 (m, 1H) 7.75-7.63 (m, 1H); $^{13}$C NMR (101 MHz, CDCl$_3$) δ 15.78, 15.85, 16.72, 21.17, 23.30, 25.22, 35.85, 35.95, 39.77, 50.79, 52.11, 52.39, 53.01, 59.13, 128.81, 130.23, 130.89, 131.51, 131.78, 133.35, 165.22, 169.50, 169.87, 207.98; HRMS calcd for C$_{24}$H$_{33}$Cl$_2$N$_3$O$_5$S$_2$Na, [M + Na]$^+$ 600.1130, found 600.1132. |
| 43 | 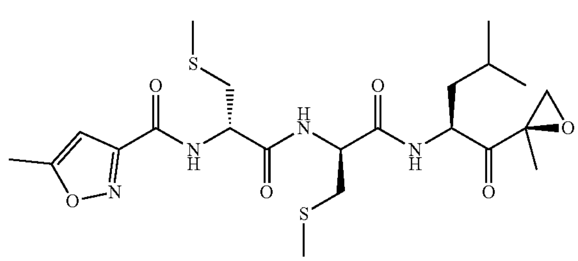 [SMILES: CSC[C@@H](NC(=O)c1cc(C)on1)C(=O)N[C@H](CSC)C(=O)N[C@@H](CC(C)C)C(=O)[C@@]1(C)CO1] | N-5-methylisoxazolyl-3-formyl-S-methyl-L-cysteinyl-S-methyl-L-cysteinyl-L-leucyl-methyloxirane<br>Yield 60%, oily liquid; $^1$H NMR (400 MHz, CDCl$_3$) δ 0.94 (dd, 6H), 1.50 (d, J = 4.1 Hz, 3H), 1.69-1.63 (m, 1H), 1.71 (d, J = 11.9 Hz, 2H), 2.13 (d, J = 12.0 Hz, 3H), 2.20 (d, 3H), 2.48 (s, J = 0.7 Hz, 3H), 2.80 (td, J = 14.2, 6.9 Hz, 1H), 3.02-2.86 (m, 4H), 3.30 (t, J = 5.5 Hz, 1H), 4.66-4.52 (m, 2H), 4.76-4.68 (m, 1H), 6.41 (dd, J = 4.4, 0.8 Hz, 1H), 6.97 (s, 1H), 7.15 (s, J = 7.4 Hz, 1H), 7.64 (s, 1H); $^{13}$C NMR (101 MHz, CDCl$_3$) δ 12.35, 15.81, 15.93, 16.72, 21.22, 23.37, 25.21, 35.90, 35.99, 39.81, 50.77,<br><br>52.06, 52.38, 52.88, 59.13, 101.29, 159.36, 169.40, |

| No. | Structure | Chemical name and analysis data |
|---|---|---|
| | | 169.91, 171.51, 207.97; HRMS calcd for $C_{22}H_{34}N_4O_6S_2Na$, [M + Na]$^+$ 537.1811, found 537.1808. |
| 44 | 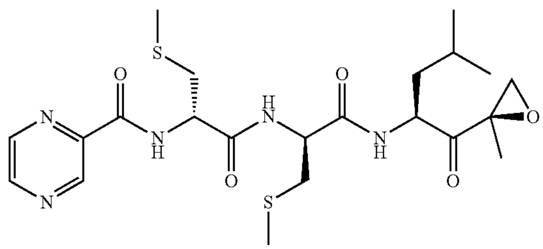 [SMILES: CSC[C@@H](NC(=O)c1cnccn1)C(=O)N[C@H](CSC)C(=O)N[C@@H](CC(C)C)C(=O)[C@@]1(C)CO1] | N-pyrazinyl-2-formyl-S-methyl-L-cysteinyl-S-methyl-L-cysteinyl-L-leucyl-methyloxirane<br>Yield 50%, oily liquid; $^1$H NMR (400 MHz, CDCl$_3$) δ 0.93 (dd, 6H), 1.26 (s, 3H), 1.61-1.54 (m, 1H), 1.67-1.61 (m, 2H), 2.06 (d, J = 15.0 Hz, 3H), 2.22 (d, J = 6.4 Hz, 3H), 2.93-2.72 (m, 2H), 3.13-2.93 (m, 3H), 3.32-3.22 (m, 1H), 4.67-4.50 (m, 2H), 4.83-4.67 (m, 1H), 8.58 (s, 1H), 8.79 (s, J = 4.2, 2.2 Hz, 1H), 9.37 (d, 1H); $^{13}$C NMR (101 MHz, CDCl$_3$) δ 15.81, 15.99, 16.70, 21.05, 21.21, 23.38, 35.91, 36.14, 39.81, 50.84, 52.10, 52.45, 60.39, 142.81, 142.88, 144.37, 147.75, 163.27, 169.50, 169.96, 208.00; HRMS calcd for $C_{22}H_{33}N_5O_5S_2Na$, [M + Na]$^+$ 534.1815, found 534.1815. |
| 45 | 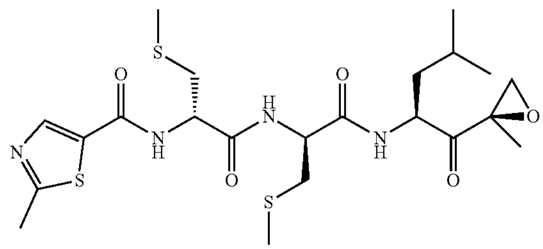 [SMILES: CSC[C@@H](NC(=O)c1cnc(C)s1)C(=O)N[C@H](CSC)C(=O)N[C@@H](CC(C)C)C(=O)[C@@]1(C)CO1] | N-2-methylthiazolyl-5-formyl-S-methyl-L-cysteinyl-S-methyl-L-cysteinyl-L-leucyl-methyloxirane<br>Yield 78%, m.p.: 150-151° C.; $^1$H NMR (400 MHz, CDCl$_3$) δ 0.93 (d, J = 4.5 Hz, 3H), 0.95 (d, 3H), 1.50 (d, 3H), 1.60-1.54 (m, 1H), 1.73-1.68 (m, 2H), 2.12 (d, 3H), 2.20 (d, 3H), 2.74 (d, J = 2.3 Hz, 3H), 2.84-2.78 (m, 1H), 2.95 (dd, J = 9.6, 4.2 Hz, 2H), 3.05-2.93 (m, 2H), 3.28 (t, J = 5.8 Hz, 1H), 4.67-4.51 (m, 2H), 4.77-4.67 (m, J = 7.7, 6.8, 5.6 Hz, 1H), 7.06 (s, 1H), 7.52 (s, 1H), 7.71 (s, 1H), 8.06 (s, 1H); $^{13}$C NMR (101 MHz, CDCl$_3$) δ 15.81, 15.99, 16.70, 21.05, 21.21, 23.38, 35.91, 36.14, 39.81, 50.84, 52.10, 52.45, 60.39, 142.81, 142.88, 144.37, 147.75, 163.27, 169.50, 169.96, 208.00; HRMS calcd for $C_{22}H_{34}N_4O_5S_3Na$, [M + Na]$^+$ 553.1583, found 553.1580. |
| 46 | 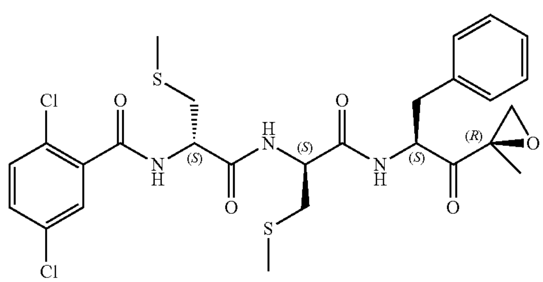 | N-2,5-dichlorophenyl-2-formyl-S-methyl-L-cysteinyl-S-methyl-L-cysteinyl-L-phenylalanyl-methyloxirane<br>Yield 78%, m.p.: 150-151° C.; $^1$H NMR (400 MHz, CDCl$_3$) δ 1.50 (s, 3H), 1.96 (s, 3H), 2.21 (s, 3H), 2.81-2.68 (m, J = 18.9, 14.0, 7.9 Hz, 2H), 2.89 (dd, J = 6.2, 1.0 Hz, 1H), 2.94-2.91 (m, 2H), 3.06 (dd, J = 13.9, 5.4 Hz, 1H), 3.16 (dd, J = 14.0, 4.5 Hz, 1H), 3.33 (d, J = 6.6 Hz, 1H), 4.52-4.46 (m, J = 7.0, 5.2 Hz, 1H), 4.75-4.68 (m, J = 13.4, 6.7 Hz, 1H), 4.84-4.78 (m, J = 11.5, 3.5 Hz, 1H), 7.15 (d, J = 8.8 Hz, 2H), 7.18 (dd, J = 4.3, 2.6 Hz, 2H), 7.21 (d, J = 3.4 Hz, 2H), 7.24-7.22 (m, 1H), 7.24 (s, 1H), 7.38 (d, J = 1.5 Hz, 2H), 7.68 (dd, J = 3.5, 2.1 Hz, 1H); $^{13}$C NMR (101 MHz, CDCl$_3$) δ 15.49, 15.70, 16.53, 35.64, 35.73, 36.80, 51.88, 52.49, 52.87, 53.24, 59.33, 127.10, 128.56, 129.08, 129.26, 130.21, 131.53, 131.82, 133.36, 135.17, 135.83, 165.23, 169.43, 169.70, 207.12; HRMS calcd for $C_{27}H_{31}Cl_2N_3O_5S_2Na$, [M + Na]$^+$ 634.0974, found 634.0974. |
| 47 | 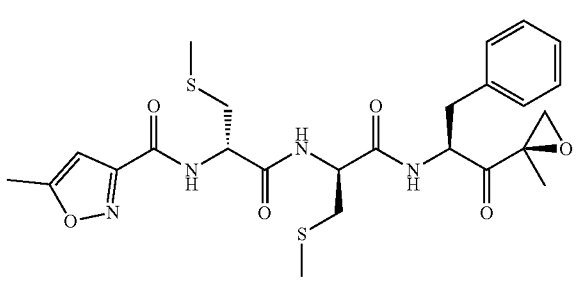 [SMILES: CSC[C@@H](NC(=O)c1cc(C)on1)C(=O)N[C@H](CSC)C(=O)N[C@@H](Cc1ccccc1)C(=O)[C@@]1(C)CO1] | N-5-methylisoxazolyl-3-formyl-S-methyl-L-cysteinyl-S-methyl-L-cysteinyl-L-phenylalanyl-methyloxirane<br>Yield 80%, m.p.: 149-150° C.; $^1$H NMR (400 MHz, CDCl$_3$) δ 1.49 (dd, J = 8.2, 2.6 Hz, 3H), 1.98 (d, J = 4.9 Hz, 1H), 2.18 (d, 3H), 2.05 (d, J = 1.9 Hz, 2H), 2.48 (dd, J = 6.2, 0.8 Hz, 3H), 2.83-2.61 (m, 3H), 2.89-2.84 (m, 1H), 2.93-2.89 (m, 1H), 3.00-2.94 (m, 2H), 3.20-3.09 (m, J = 12.9, 7.9, 4.8 Hz, 1H), 3.35-3.29 (m, 1H), 4.50 (dtd, J = 12.4, 7.1, 5.4 Hz, 1H), 4.73-4.59 (m, 1H), 4.88-4.74 (m, 1H), 6.40 (d, J = 13.2, 0.9 Hz, 1H), 7.15-7.09 (m, 1H), 7.20-7.14 (m, 2H), 7.25-7.20 (m, J = 7.5, 3.7, 2.1 Hz, 1H), 7.32-7.27 (m, 2H), 7.64 (d, J = 7.0 Hz, 1H); $^{13}$C NMR (101 MHz, CDCl$_3$) δ 12.36, 15.56, 15.86, 16.52, 35.67, 35.83, 36.88, 51.72, 51.83, 52.18, 52.56, 53.24, 59.31, 101.30, 127.14, 128.58, 128.59, 129.28, 129.31, 135.79, 157.90, 159.36, 169.35, 169.71, 171.54, 207.06; HRMS calcd for $C_{25}H_{32}N_4O_6S_2Na$, [M + Na]$^+$ 571.1655, found 571.1656. |

| No. | Structure | Chemical name and analysis data |
|---|---|---|
| 48 | 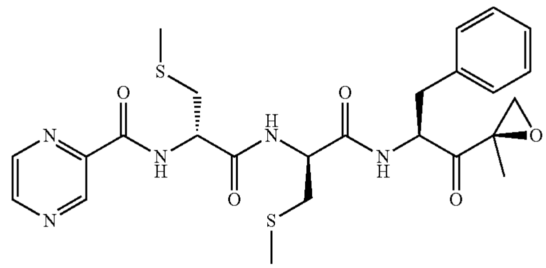 [SMILES: CSC[C@@H](NC(=O)c1cnccn1)C(=O)N[C@H](CSC)C(=O)N[C@@H](Cc1ccccc1)C(=O)[C@@]1(C)CO1] | N-pyrazinyl-2-formyl-S-methyl-L-cysteinyl-S-methyl-L-cysteinyl-L-phenylalanyl-methyloxirane<br>Yield 78%, oily liquid; $^1$H NMR (400 MHz, CDCl$_3$) δ 1.24 (s, 3H), 1.99 (d, J = 4.3 Hz, 1H), 2.04 (t, 2H), 2.18 (s, 3H), 2.85-2.61 (m, 2H), 2.96-2.85 (m, J = 10.5, 6.7, 6.0, 4.3 Hz, 2H), 3.06-2.96 (m, 2H), 3.21-3.10 (m, 1H), 3.33-3.27 (m, J = 12.1, 4.8 Hz, 1H), 4.57-4.44 (m, J = 7.0, 5.1, 3.6 Hz, 1H), 4.84-4.63 (m, 2H), 7.14 (dd, J = 5.0, 2.2 Hz, 1H), 7.18-7.16 (m, 1H), 7.22-7.19 (m, 1H), 7.23 (dd, J = 6.8, 1.9 Hz, 1H), 7.32-7.27 (m, 1H), 8.62-8.53 (m, 1H), 8.82-8.75 (m, 1H), 9.41-9.32 (m, 1H); $^{13}$C NMR (101 MHz, CDCl$_3$) δ 15.55, 15.91, 16.52, 35.74, 36.10, 36.88, 51.72, 53.23, 59.27, 59.31, 60.40, 127.11, 127.15, 128.54, 128.57, 129.29, 135.73, 142.83, 143.67, 144.33, 147.73, 163.23, 163.41, 169.72, 207.09; HRMS calcd for C$_{25}$H$_{31}$N$_5$O$_5$S$_2$Na, [M + Na]+ 568.1658, found 568.1660. |
| 49 | 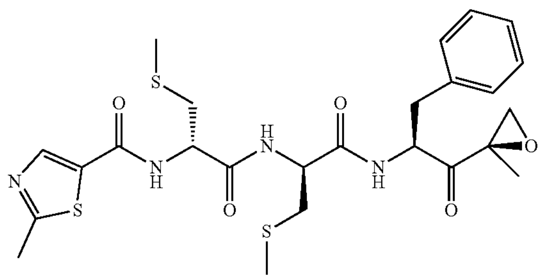 [SMILES: CSC[C@@H](NC(=O)c1cnc(C)s1)C(=O)N[C@H](CSC)C(=O)N[C@@H](Cc1ccccc1)C(=O)[C@@]1(C)CO1] | N-2-methylthiazolyl-5-formyl-S-methyl-L-cysteinyl-S-methyl-L-cysteinyl-L-phenylalanyl-methyloxirane<br>Yield 80%, m.p.: 73-74° C.; $^1$H NMR (400 MHz, CDCl$_3$) δ 1.49 (d, 3H), 1.96 (s, 2H), 2.03 (s, 1H), 2.20 (d, 3H), 2.73 (s, 1H), 2.74 (s, 3H), 2.87-2.77 (m, 2H), 2.94-2.88 (m, 2H), 3.02-2.95 (m, 1H), 3.16 (dt, J = 13.9, 5.2 Hz, 1H), 3.31 (dd, J = 4.7, 2.3 Hz, 1H), 4.58-4.45 (m, 1H), 4.72-4.59 (m, 1H), 4.87-4.75 (m, J = 13.6, 8.5, 4.7 Hz, 1H), 7.15-7.01 (m, 1H), 7.20-7.15 (m, 3H), 7.25-7.21 (m, 2H), 7.31-7.27 (m, 2H), 8.08 (s, 1H); $^{13}$C NMR (101 MHz, CDCl$_3$) δ 15.56, 15.68, 16.52, 19.70, 35.73, 36.04, 36.88, 51.98, 52.33, 52.49, 53.23, 59.31, 127.15, 127.17, 128.59, 129.28, 129.33, 132.94, 135.77, 143.73, 160.54, 169.68, 169.75, 170.95, 207.19; HRMS calcd for C$_{25}$H$_{32}$N$_4$O$_5$S$_3$Na, [M + Na]$^+$ 587.1427, found 587.1428. |
| 50 | 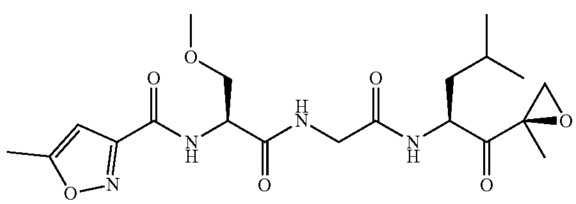 [SMILES: COC[C@H](NC(=O)c1cc(C)on1)C(=O)NCC(=O)N[C@@H](CC(C)C)C(=O)[C@@]1(C)CO1] | N-5-methylisoxazolyl-3-formyl-O-methyl-L-seryl-glycyl-L-leucyl-methyloxirane<br>Yield 80%, m.p.: 47.7-49.1° C.; $^1$H NMR (400 MHz, CDCl$_3$) δ 0.91 (s, 6H), 1.23 (d, J = 10.5 Hz, 1H), 1.49 (s, 3H), 1.71-1.56 (m, 2H), 2.48 (s, J = 0.8 Hz, 3H), 2.88 (d, J = 4.9 Hz, 1H), 3.32 (d, J = 11.9, 5.0 Hz, 1H), 3.42 (s, J = 1.1 Hz, 3H), 3.67-3.55 (m, 1H), 3.97-3.73 (m, 2H), 4.21-3.99 (m, 1H), 4.76-4.52 (m, 2H), 6.42 (s, J = 2.6, 0.9 Hz, 1H), 6.65 (s, J = 8.3 Hz, 1H), 7.12 (s, 1H), 7.65 (s, J = 6.0 Hz, 1H); $^{13}$C NMR (101 MHz, CDCl$_3$) δ 12.34, 16.66, 21.19, 23.33, 25.04, 39.92, 43.02, 50.14, 52.42, 53.19, 59.05, 59.35, 71.48, 101.38, 158.00, 159.49, 168.54, 169.62, 171.49, 208.78; HRMS calcd for C$_{20}$H$_{30}$N$_4$O$_7$Na, [M + Na]$^+$ 461.2006, found 461.2005. |
| 51 | 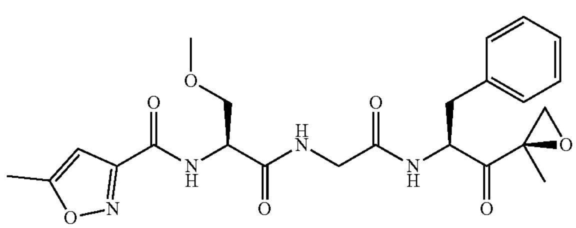 [SMILES: COC[C@H](NC(=O)c1cc(C)on1)C(=O)NCC(=O)N[C@@H](Cc1ccccc1)C(=O)[C@@]1(C)CO1] | N-5-methylisoxazolyl-3-formyl-O-methyl-L-seryl-glycyl-L-phenylalanyl-methyloxirane<br>Yield 85%, m.p.: 54-55° C.; $^1$H NMR (400 MHz, CDCl$_3$) δ 1.50 (s, 3H), 2.49 (s, 3H), 2.87-2.76 (m, J = 13.8, 8.1, 3.1 Hz, 1H), 2.90 (d, J = 4.9 Hz, 1H), 3.11 (dd, J = 13.9, 5.1 Hz, 1H), 3.30 (dd, J = 9.5, 4.9 Hz, 1H), 3.39 (s, 3H), 3.61-3.47 (m, 1H), 4.04-3.78 (m, 3H), 4.74-4.60 (m, 1H), 4.91-4.76 (m, 1H), 6.41 (s, J = 0.8 Hz, 1H), 6.71 (d, J = 7.9 Hz, 1H), 7.09-7.01 (m, J = 13.2, 7.7 Hz, 1H), 7.20-7.10 (m, 2H), 7.25-7.20 (m, 1H), 7.29 (d, 1H), 7.63 (d, J = 7.0 Hz, 1H); $^{13}$C NMR (101 MHz, CDCl$_3$) δ 12.34, 16.47, 37.08, 42.99, 52.48, 52.65, 52.95, 59.22, 59.27, 71.31, 101.38, 127.13, 128.56, 129.32, 135.58, 158.01, 159.48, 168.30, 169.65, 171.48, 207.55; HRMS calcd for C$_{23}$H$_{28}$N$_4$O$_7$Na, [M + Na]$^+$ 495.1850, found 495.1848. |

| No. | Structure | Chemical name and analysis data |
|---|---|---|
| 52 | 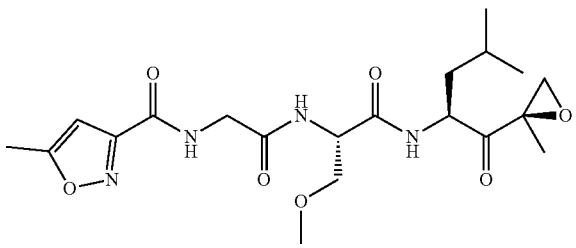 [SMILES: COC[C@H](NC(=O)CNC(=O)c1cc(C)on1)C(=O)N[C@@H](CC(C)C)C(=O)[C@@]1(C)CO1] | N-5-methylisoxazolyl-3-formyl-glycyl-O-methyl-L-seryl-L-leucyl-methyloxirane<br>Yield 80%, oily liquid; $^1$H NMR (400 MHz, CDCl$_3$)<br>δ 0.92 (s, 6H), 1.50 (s, 3H), 1.59-1.52 (m, 1H), 1.72-1.59 (m, J = 19.6, 15.6, 9.3, 4.0 Hz, 2H), 2.47 (s, 3H), 2.88 (d, J = 5.0 Hz, 1H), 3.27 (d, J = 5.0 Hz, 1H), 3.33 (s, 1H), 3.39 (s, J = 5.8 Hz, 3H), 3.80-3.72 (m, J = 9.1, 3.9 Hz, 1H), 4.14-4.09 (m, 2H), 4.62-4.53 (m, 2H), 6.42 (s, J = 0.8 Hz, 1H), 6.93 (d, J = 6.3 Hz, 1H), 6.99 (d, J = 8.2 Hz, 1H), 7.58 (s, J = 5.3 Hz, 1H); $^{13}$C NMR (101 MHz, CDCl$_3$) δ 12.32, 16.73, 21.20, 23.31, 25.18, 39.82, 42.95, 50.77, 52.09, 52.42, 59.04, 59.13, 71.34, 101.36, 158.04, 159.74, 168.11, 169.90, 171.33, 208.20; HRMS calcd for C$_{20}$H$_{30}$N$_4$O$_7$Na, [M + Na]+ 461.2006, found 461.2005. |
| 53 | 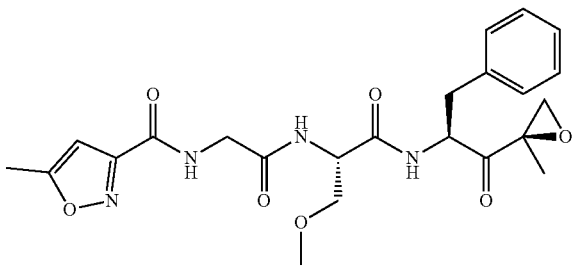 [SMILES: COC[C@H](NC(=O)CNC(=O)c1cc(C)on1)C(=O)N[C@@H](Cc1ccccc1)C(=O)[C@@]1(C)CO1] | N-5-methylisoxazolyl-3-formyl-glycyl-O-methyl-L-seryl-L-phenylalanyl-methyloxirane<br>Yield 80%, oily liquid; $^1$H NMR (400 MHz, CDCl$_3$)<br>δ 1.48 (s, J = 11.6 Hz, 3H), 2.47 (s, 3H), 2.85-2.77 (m, 1H), 2.91 (dd, J = 4.9, 2.5 Hz, 1H), 3.17-3.10 (m, 1H), 3.23 (s, 1H), 3.29 (s, 3H), 3.34 (dd, J = 92, 7.5 Hz, 1H), 3.77-3.60 (m, J = 19.1, 9.2, 3.9 Hz, 1H), 4.13-4.03 (m, 2H), 4.56-4.39 (m, J = 18.2, 7.0, 3.9 Hz, 1H), 4.82-4.71 (m, 1H), 6.39 (s, J = 0.8 Hz, 1H), 6.82 (s, J = 6.9 Hz, 1H), 7.08 (s, J = 7.7 Hz, 1H), 7.18-7.12 (m, 2H), 7.25-7.20 (m, 1H), 7.31-7.27 (m, 2H), 7.52 (s, 1H); $^{13}$C NMR (101 MHz, CDCl$_3$) δ 12.32, 16.57, 36.79, 42.84, 51.92, 52.54, 53.17, 59.03, 59.32, 71.06, 101.37, 127.12, 128.55, 129.33, 135.61, 158.05, 159.68, 168.11, 169.68, 171.33, 207.11; HRMS calcd for C$_{23}$H$_{28}$N$_4$O$_7$Na, [M + Na]$^+$ 495.1850, found 495.1848. |
| 54 | 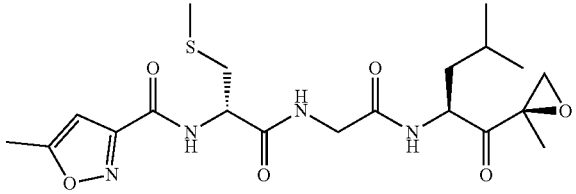 [SMILES: CSC[C@@H](NC(=O)c1cc(C)on1)C(=O)NCC(=O)N[C@@H](CC(C)C)C(=O)[C@@]1(C)CO1] | N-5-methylisoxazolyl-3-formyl-S-methyl-L-cysteinyl-glycyl-L-leucyl-methyloxirane<br>Yield 80%, m.p.: 58.4-59.8° C.; $^1$H NMR (400 MHz, CDCl$_3$) δ 0.91 (dd, 6H), 1.26 (dt, J = 7.1, 2.6 Hz, 1H), 1.36-1.30 (m, 1H), 1.48 (s, 3H), 1.69-1.58 (m, 1H), 2.19 (s, 3H), 2.48 (s, J = 0.8 Hz, 3H), 2.88 (d, J = 5.8 Hz, 1H), 3.00 (qd, J = 13.9, 6.6 Hz, 2H), 3.31 (d, J = 4.9 Hz, 1H), 3.90 (dd, J = 16.9, 5.2 Hz, 1H), 4.11-4.01 (m, 1H), 4.74-4.51 (m, 2H), 6.41 (dd, J = 4.4, 0.9 Hz, 1H), 6.71 (d, J = 8.1 Hz, 1H), 7.19 (d, J = 5.5 Hz, 1H), 7.70 (d, J = 7.0 Hz, 1H); $^{13}$C NMR (101 MHz, CDCl$_3$) δ 12.36, 15.89, 16.70, 21.16, 23.32, 25.09, 35.77, 39.76, 43.06, 50.38, 52.46, 52.54, 59.10, 101.32, 157.91, 159.49, 168.43, 169.97, 171.53, 208.73; HRMS calcd for C$_{20}$H$_{30}$N$_4$O$_6$SNa, [M + Na]$^+$ 477.1778, found 477.1781. |
| 55 | 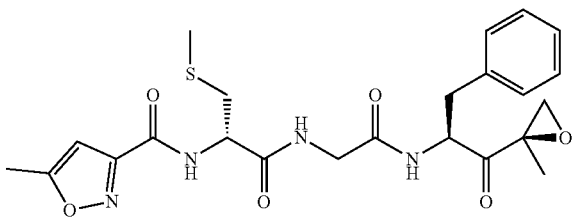 [SMILES: CSC[C@@H](NC(=O)c1cc(C)on1)C(=O)NCC(=O)N[C@@H](Cc1ccccc1)C(=O)[C@@]1(C)CO1] | N-5-methylisoxazolyl-3-formyl-S-methyl-L-cysteinyl-glycyl-L-phenylalanyl-methyloxirane<br>Yield 78%, oily liquid; $^1$H NMR (400 MHz, CDCl$_3$)<br>δ 1.47 (s, J = 4.4 Hz, 3H), 2.17 (s, J = 3.2 Hz, 3H), 2.47 (s, J = 0.8 Hz, 3H), 2.85-2.77 (m, 1H), 2.91-2.88 (m, 1H), 3.02-2.92 (m, 2H), 3.12 (dd, J = 13.9, 5.0 Hz, 1H), 3.29 (d, J = 5.5 Hz, 1H), 3.82 (dd, 1H), 3.95 (dd, 1H), 4.68 (p, J = 6.8 Hz, 1H), 4.82 (td, J = 7.9, 5.0 Hz, 1H), 6.39 (s, J = 0.9 Hz, 1H), 6.76 (d, J = 7.6 Hz, 1H), 7.16-7.11 (m, 3H), 7.25-7.21 (m, 1H), 7.28 (d, J = 1.6 Hz, 1H), 7.69 (d, J = 7.2 Hz, 1H); $^{13}$C NMR (101 MHz, CDCl3) δ 12.35, 15.83, 16.49, 35.77, 36.95, 43.00, 52.32, 52.51, 52.82, 59.26, 101.32, 127.14, 128.57, 129.28, 135.61, 157.93, 159.44, 168.17, 169.98, 171.50, 207.58; HRMS calcd for C$_{23}$H$_{28}$N$_4$O$_6$SNa, [M + Na]+ 7511.1621, found 511.1619. |

| No. | Structure | Chemical name and analysis data |
|---|---|---|
| 56 | 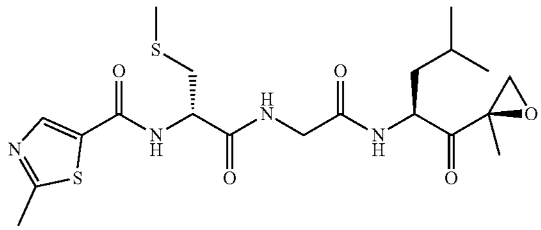 [SMILES: CSC[C@@H](NC(=O)c1cnc(C)s1)C(=O)NCC(=O)N[C@@H](CC(C)C)C(=O)[C@@]1(C)CO1] | N-2-methylthiazolyl-5-formyl-S-methyl-L-cysteinyl-glycyl-L-leucyl-methyloxirane<br>Yield 80%, oily liquid; $^1$H NMR (400 MHz, CDCl$_3$)<br>δ 0.91 (d, J = 5.7 Hz, 3H), 0.93 (d, J = 3.4 Hz, 3H), 1.51 (s, 3H), 1.57-1.51 (m, 1H), 1.71-1.60 (m, 2H), 2.18 (s, 3H), 2.73 (s, 3H), 2.88 (dd, J = 7.8, 5.1 Hz, 2H), 2.98-2.94 (m, 1H), 3.36-3.24 (m, 1H), 3.89 (dd, 1H), 4.08 (dd, 1H), 4.73-4.56 (m, 2H), 6.82 (s, J = 8.0 Hz, 1H), 7.34 (s, J = 5.4 Hz, 1H), 8.10 (s, 1H); $^{13}$C NMR (101 MHz, CDCl$_3$) δ 15.70, 16.72, 19.66, 21.16, 23.33, 25.14, 35.77, 39.70, 43.09, 50.50, 52.46, 52.63, 59.11, 132.98, 143.84, 160.81, 168.47, 170.56, 171.00, 208.93; HRMS calcd for C$_{20}$H$_{30}$N$_4$O$_5$S$_2$Na, [M + Na]$^+$ 493.1549, found 493.1547. |

Part II Determination of Proteasome Inhibition Activity

I. Proteasome Inhibition Activity

The present invention uses a fluorescent polypeptide substrate Suc-Leu-Leu-Val-Tyr-AMC (abbreviated as Suc-LLVY-AMC, Suc stands for succinyl group, AMC stands for 7-amide-4-methylcoumarin) to determine the chymotrypsin-like enzyme activity of the proteasome.

The proteasome used in the present invention is human red blood cell 20S proteasome, and the enzymes, fluorescent substrates and test buffers are all purchased from Enzo company. The experimental system is 16 μL, wherein the substrate is 8 μL, the proteasome is 4 μL (0.8 ng), the final concentration is 50 μM, the drug (inhibitor) is 4 μL, the final concentration is $2 \times 10^{-6}$ M-$4.88 \times 10^{-10}$ M, the last concentration is 0 M, the actual preparation concentration is $8 \times 10^{-6}$ M-$1.95 \times 10^{-9}$ M, and the last concentration is 0 M. The specific experiment process is as follows:

1. Drug Preparation:

The drug is weighed and added to DMSO to dissolve to a concentration of $10^{-2}$ M. 2 μL of the drug solution is pipetted and added to 98 μL of DMSO to obtain a drug solution with the concentration of $2 \times 10^{-4}$ M. Then 8 μL of the drug solution with the concentration of $2 \times 10^{-4}$ M is pipetted and added to 198 μL of H$_2$O to obtain a drug solution with the concentration of $8 \times 10^{-6}$ M. Drugs with the concentrations of $2 \times 10^{-6}$ M, $5 \times 10^{-7}$ M, $1.25 \times 10^{-7}$ M, $3.12 \times 10^{-8}$ M, $7.8 \times 10^{-9}$ M, and $1.95 \times 10^{-9}$ M are obtained by the same method, and the last concentration 0 M means drug-free.

2. Substrate Preparation:

25 mg of fluorescent polypeptide substrate is dissolved in 654 μL of DMSO to obtain a 50 mM stock solution. The stock solution is stored at −20° C., and diluted 500 times when in use. 8 μL of the diluted stock solution is added to each sample so that the final substrate concentration in the reaction system is 50 μM.

3. Reaction System Preparation:

The 20S proteasome is diluted with a buffer solution to a concentration of 2 ng/μL from 8 ng/μL, and the diluted proteasome solution is added to a 384-well fluorescence microplate, 4 μL each. Then 4 μL of the sample to be tested is added to each well, the marketed drug Carfilzomib is used as the positive control drug, and reaction is performed at 37° C. for 15 min. After the reaction is complete, 8 μL of fluorescent substrate is added to each well, and the reaction is performed for 1 h at 37° C. in the dark. A 360 nm/460 nm fluorescence microplate reader (BMG LABTECH POLAR-star OPTIMA Microplate Reader) is used to test the fluorescence value.

4. Data Processing:

The fluorescence values of the products obtained under the action of the drugs of different concentrations after subtracting the substrate are calculated. The IC$_{50}$ concentration of the drug to inhibit the proteasome is calculated by the GraphPad Prism software.

| Compound No. | IC$_{50}$ (nM) |
|---|---|
| 30 | 59.31 |
| 31 | 90.38 |
| 32 | 2797 |
| 33 | 31.66 |
| 34 | 91.85 |
| 35 | 1275 |
| 36 | 41.91 |
| 37 | 93.35 |
| 38 | >2000 |
| 39 | 167.2 |
| 40 | 34.24 |
| 41 | 751.70 |
| 42 | 15.88 |
| 43 | 16.43 |
| 44 | 1484 |
| 45 | 71.49 |
| 46 | 50.82 |
| 47 | 27.32 |
| 48 | >2000 |
| 49 | 35.53 |
| 50 | 69.22 |
| 51 | 57.04 |
| 52 | 1494 |
| 53 | 1319 |
| 54 | 27.15 |
| 55 | 23.56 |
| 56 | 123.6 |
| Oprozomib | 235.2 |

II. Cell Strain Inhibition Activity

The test solution used in the present invention is a single solution cell proliferation test kit from Promega company; and the cells used are U266 and RPMI8226. The experimental system is 110 μL, containing 90 μL of cell suspension, 10 μL of test solution, and 10 μL of drug (inhibitor). The final concentration is $4.54 \times 10^{-8}$ M-$1.77 \times 10^{-9}$ M, the last concentration is 0 M, the actual preparation concentration is $5 \times 10^{-7}$ M-$1.95 \times 10^{-8}$ M, and the last concentration is 0 M. The specific experiment process is as follows:

1. Drug Preparation:

The drug is accurately weighed and added to DMSO to dissolve to a concentration of $10^{-2}$ M. 1 μL of the drug solution is pipetted and added to 199 μL of DMSO to obtain a drug solution with the concentration of $5\times10^{-5}$ M. Then 3.3 μL of the drug solution with the concentration of $5\times10^{-5}$ M is pipetted and added to 326.7 μL of serum-free RPMI1640 medium to obtain a drug solution with the concentration of $5\times10^{-7}$ M. The drug solution receives gradient dilution by 1.5 times to obtain drugs with the concentrations of $3.3\times10^{+7}$ M, $2.2\times10^{-7}$ M, $1.48\times10^{-7}$ M, $9.87\times10^{+8}$ M, $6.58\times10^{-8}$ M, $4.38\times10^{-8}$ M, $2.92\times10^{-8}$ M and $1.95\times10^{-8}$ M, and the last concentration 0 M means drug-free.

2. Cell Suspension Preparation:

After the cells are counted separately, dilution and preparation are performed so that the number of U266 is $1\times10^4$ cells/well, and the number of RPMI8226 is $1\times10^4$ cells/well.

3. Reaction System Preparation:

90 μL of cell suspension is added to each well of a 96-well fluorescence microplate, and incubated for 24 h. Then 10 μL of the sample to be tested is added to each well, the drug Oprozomib is used as the positive control drug, and incubation is performed for 24 h. After the reaction is complete, 10 μL of test solution is added to each well and incubation is performed for 2-3 h. The absorbance is tested with a 490 nm fluorescence microplate reader (BMG LABTECH POLARstar OPTIMA Microplate Reader).

4. Data Processing:

The absorbances of the products obtained under the action of the drugs of different concentrations after subtracting the substrate are calculated. The $IC_{50}$ concentration (nM) of the drugs to cytotoxicity is calculated by the GraphPad Prism software.

The results of some compounds are as follows:

| No. | U266B1 | RPMI8226 |
| --- | --- | --- |
| 30 | 25.19 | NT |
| 31 | 26.41 | NT |
| 32 | 13677 | NT |
| 33 | 31.66 | 51.87 |
| 34 | 28.05 | 29.6 |
| 35 | 422 | NA |
| 36 | 44.48 | NT |
| 37 | 51.52 | NT |
| 38 | NA | NT |
| 39 | 54.21 | 82.28 |
| 40 | 58.48 | NA |
| 41 | 159.6 | 55.34 |
| 42 | 73.56 | 50.75 |
| 43 | 36.07 | 33.23 |
| 44 | NA | NA |
| 45 | 55.91 | 56.25 |
| 46 | 59.31 | 58.51 |
| 47 | 44.16 | 32.78 |
| 48 | NA | NA |
| 49 | 35.92 | 42.09 |
| 50 | NT | 70.24 |
| 51 | NT | 42.48 |
| 52 | NT | >100 |
| 53 | NT | NT |
| 54 | NT | 66.36 |
| 55 | NT | 47.48 |
| 56 | NT | >100 |
| Oprozomib | 22.36 | 31.50 |

NT: Not tested;
NA: Not active

III. Primary Cytotoxicity in Patients with Multiple Myeloma

In the present invention, blood cells from patients with multiple myeloma and blood cells from healthy volunteers are used to test the toxicity of candidate compounds. The test solution is a single solution cell proliferation test kit from Promega company. The cells used are CD138+ cells selected from the patients with multiple myeloma and monocytes from the blood of the healthy volunteers. The experimental system is 110 μL, containing 90 μL of cell suspension, 10 μL of test solution, and 10 μL of drug (inhibitor). The final concentration is $4.54\times10^{-8}$ M $1.77\times10^{-9}$ M, the last concentration is 0 M, the actual preparation concentration is $5\times10^{-7}$ M-$1.95\times10^{-8}$ M, and the last concentration is 0 M. The specific experiment process is as follows:

1. Drug Preparation:

The drug is accurately weighed and added to DMSO to dissolve to a concentration of $10^{-2}$ M. 1 μL u of the drug solution is pipetted and added to 199 μL of DMSO to obtain a drug solution with the concentration of $5\times10^{-5}$ M. Then 3.3 μL of the drug solution with the concentration of $5\times10^{-5}$ M is pipetted and added to 326.7 μL of serum-free RPMI1640 medium to obtain a drug solution with the concentration of $5\times10^{-7}$ M. The drug solution receives gradient dilution by 1.5 times to obtain drugs with the concentrations of $3.3\times10^{-7}$ M, $2.2\times10^{-7}$ M, $1.48\times10^{-7}$ M, $9.87\times10^{-8}$ M, $6.58\times10^{-8}$ M, $4.38\times10^{-8}$ M, $2.92\times10^{-8}$ M and $1.95\times10^{-8}$ M, and the last concentration 0 M means drug-free.

2. Cell Suspension Preparation:

After the cells are counted separately, dilution and preparation are performed so that the number of CD138+ cells is $1\times10^4$ cells/well, and the number of monocytes is $1\times10^4$ cells/well.

3. Reaction System Preparation:

90 μL of cell suspension is added to each well of a 96-well fluorescence microplate, and incubated for 24 h. Then 10 μL of the sample to be tested is added to each well, the drug Oprozomib is used as the positive control drug, and incubation is performed for 24 h. After the reaction is complete, 10 μL of test solution is added to each well and incubation is performed for 2-3 h. The absorbance is tested with a 490 nm fluorescence microplate reader (BMG LABTECH POLARstar OPTIMA Microplate Reader).

4. Data Processing:

The absorbances of the products obtained under the action of the drugs of different concentrations after subtracting the substrate are calculated. The $IC_{50}$ concentration (nM) of the drugs to cytotoxicity is calculated by the GraphPad Prism software.

The results of some compounds are as follows:

|  | Oprozomib | 50 | 51 |
| --- | --- | --- | --- |
| Patient 1 | 53.04 | 10.04 | 36.05 |
| Patient 2 | 70.94 | 11.04 | 52.63 |
| Healthy volunteer 3 | 598.23 | >2000 | >2000 |
| Healthy volunteer 3 | 807.42 | >2000 | >2000 |

NA: Not active

IV. Pharmacodynamic (PD) Determination of Candidate Compounds

The preparation method of an intragastric administration solution is: A certain amount of the substance to be tested is precisely weighed and added into a glass bottle, and a certain volume of DMSO is precisely added to prepare a stock solution with a concentration of 20.0 mg·mL$^{-1}$. Then the stock solution is diluted with a polyethylene glycol 400 (PEG400) and citric acid buffer (pH=2.7) (1:1, v:v). The diluted solution is dissolved by ultrasound to make a dosing solution with the concentration of 1.00 mg·mL$^{-1}$. 24 ICR mice, weighing 18-20 g, are randomly divided into 4 groups. The 1.00 mg·mL$^{-1}$ candidate compound and Oprozomib are administered intragastrically to the mice as per 10.00 mg·kg$^{-1}$. Blood samples are collected before administration (0 min) and 2 min, 5 min, 15 min, 30 min, 1 h, 2 h, 4 h, 8 h and 12 h after administration, and about 0.200 mL of blood is collected from the orbit. The blood samples are placed in test tubes containing EDTA-K$_2$, and centrifuged at high speed (7800×g) for 5 min, and then the plasma is separated and stored at −15° C. to −35° C. Analysis and test are performed in accordance with the instructions of the Proteasome-Glo test kit from Technical Bulletin company. Data is collected with BMG LAB TECH software, and analysis and drawing are performed with GraphPad Prism 5.

Determination Method:
1. 100 µL of whole blood is taken from each mouse. 500 µL of PBS is added to wash the cells. The plasma is removed by centrifuging (3000 rpm, 5 min, 4° C.), and the process is repeated twice. The solution is washed and then resuspended with 500 µL of PBS.
2. The resuspended stock solution is diluted 5 times with PBS in two parallel gradients, and the diluted solution is added to a 384-well plate, 20 µL/well.
3. After 20 µL of proteasome-Glo detection buffer (CHTL) is added to each well, the proteasome-Glo Kinet program in the microplate reader is operated, and testing is performed once every 1 min for a total of 60 min.
4. 100 µL of the resuspended blood cells are taken. 100 µL of RIPA lysis buffer (containing 1% protease inhibitor) is added. The blood cells are lysed on ice (vortex oscillation is performed once every 5 min). Centrifugation is performed after 20 min (12500 rpm, 30 min, 4° C.).
5. After centrifugation, the supernatant (4 µL) is taken and diluted 5 times (16 µL) with RIPA lysis buffer (without protease inhibitors) for total protein quantification. The BCA method is used, that is, 5 µL of the solution to be tested and 100 µL of the prepared BCA solution are added to each well of a 96-well plate, and two sets of parallel are made for each sample. After mixing by vortex, incubation is performed at 37° C. for 30 min. The BCA protein program in the microplate reader is operated for direct test.

The pharmacodynamic results of the candidate compounds in ICR mice are shown in FIG. 1.

Part III Evaluation of the Efficacy of Candidate Compounds in Nude Mice $1×10^7$ multiple myeloma RPMI-8226-leu cells are injected into the armpits of nude mice. After the tumor grows to an average volume of 50-100 mm$^3$, the animals are randomly grouped according to the tumor volume and then administered. The 24 nude mice are divided into 7 groups: solvent control group (Control), positive control Oprozomib 50 mg/kg (1 time a day) group, compound 50 100 mg/kg b.i.d. (1 time a day) group, and compound 51 50 mg/kg (1 time a day) group, 5 mice in each group. Each group is given the test substances of the corresponding concentrations in the tail vein at a dosage of 10 mL/kg, and Oprozomib and compounds 50 and 51 are administered in the order of d1, d2, d8, d9, d15 and d16 for 21 days.

The tumor volume is weighed and measured 2 times a week. The relative tumor volume (RTV) and relative tumor proliferation rate (T/C) are calculated, and statistical analysis is performed by SPSS 19.0 software. The relative tumor volume (RTV), relative tumor proliferation rate (T/C) and tumor inhibition rate (IR) are calculated, and statistical testing is performed. The calculation formula is as follows:

TV (tumor volume)=½×a×b$^2$, where $a$ and $b$ respectively represent the length and width of the tumor; (1)

RTV (relative tumor volume)=$V_t/V_0$, where $V_0$ is the tumor volume measured during group administration (i.e. d0), and $V_t$ is the tumor volume during each measurement; (2)

T/C (%)=$T_{RTV}/C_{RTV}$×100%, where $T_{RTV}$ is the RTV of the treatment group, and $C_{RTV}$ is the RTV of the solvent control group; (3)

IR (%)=100% T/C. (4)

Preparation Method of Compound Solution:
Preparation of 5% Sulfobutyl-β-Cyclodextrin:
2.500 g of sulfobutyl-β-cyclodextrin powder is weighed and added into a beaker. 50 mL of citric acid buffer is pipetted into a beaker. The solution is transferred to a container after the powder is dissolved.

Preparation of Compound 50:
10 mg of compound 50 powder is weighed and added into a 4 mL centrifuge tube. 5% sulfobutyl-β-cyclodextrin is added to the compound 50 powder to 1 mL to obtain a 10 mg/mL compound 50 test substance solution. A certain amount of the 10 mg/mL compound 50 test substance solution is taken and diluted with 5% sulfobutyl-β-cyclodextrin to a 5 mg/mL test substance solution.

Preparation of Compound 51:
10 mg of compound 51 powder is weighed and added into a 4 mL centrifuge tube. 5% sulfobutyl-β-cyclodextrin is added to the compound 51 powder to 1 mL for complete dissolution by ultrasound to obtain a 10 mg/mL compound 51 test substance solution. A certain amount of the 10 mg/mL compound 51 test substance solution is taken and diluted with 5% sulfobutyl-β-cyclodextrin to a 5 mg/mL test substance solution.

Preparation of Oprozomib:
10 mg of Oprozomib powder is weighed and added into a 4 mL centrifuge tube. 5% sulfobutyl-β-cyclodextrin is added to the Oprozomib powder to 1 mL to obtain a 10 mg/mL Oprozomib test substance solution. A certain amount of the 10 mg/mL Oprozomib test substance solution is taken and diluted with 5% sulfobutyl-β-cyclodextrin to a 5 mg/mL test substance solution.

Figure 2:
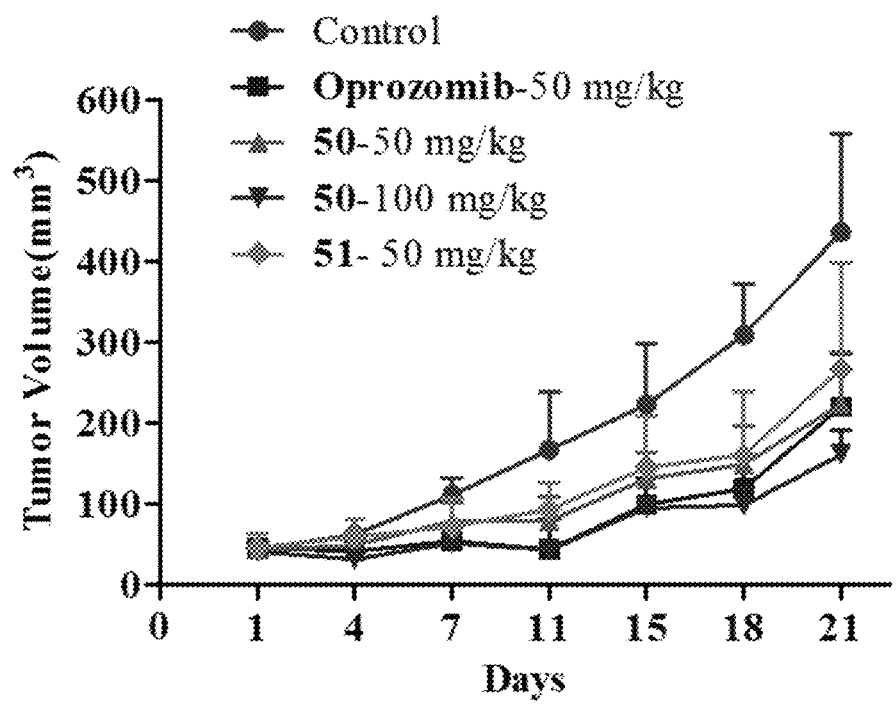
FIG. 2 Results of the drug effect of the compound of the present invention in nude mice.
Figure 3:
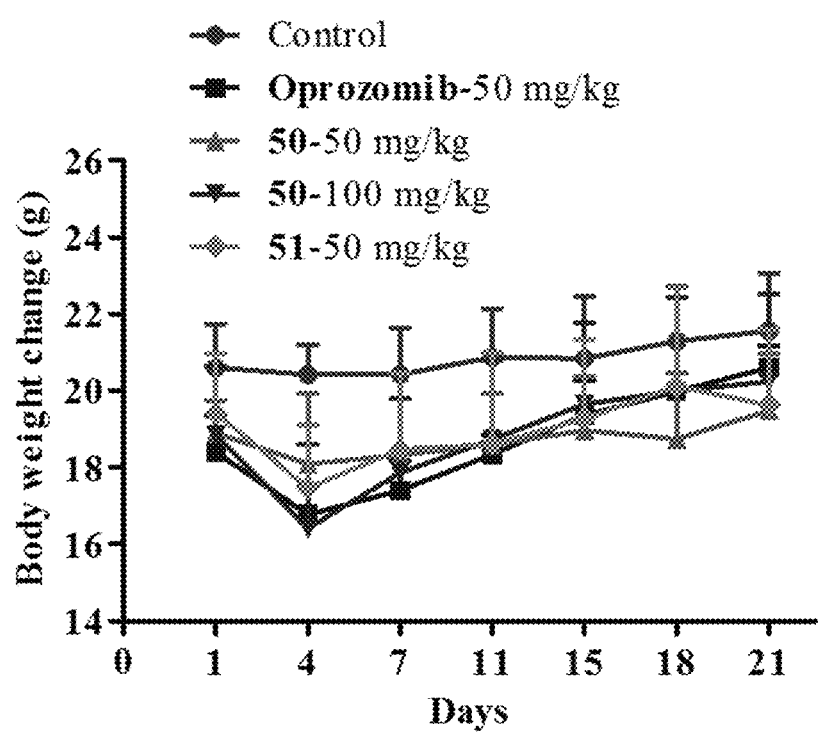
FIG. 3 Results of changes in body weight after continuous administration of the compound of the present invention to nude mice.

The results of the in vivo efficacy of the candidate compounds in nude mice are shown in FIG. 2, and the results of the body weight change of the candidate compounds in nude mice after continuous administration are shown in FIG. 3.

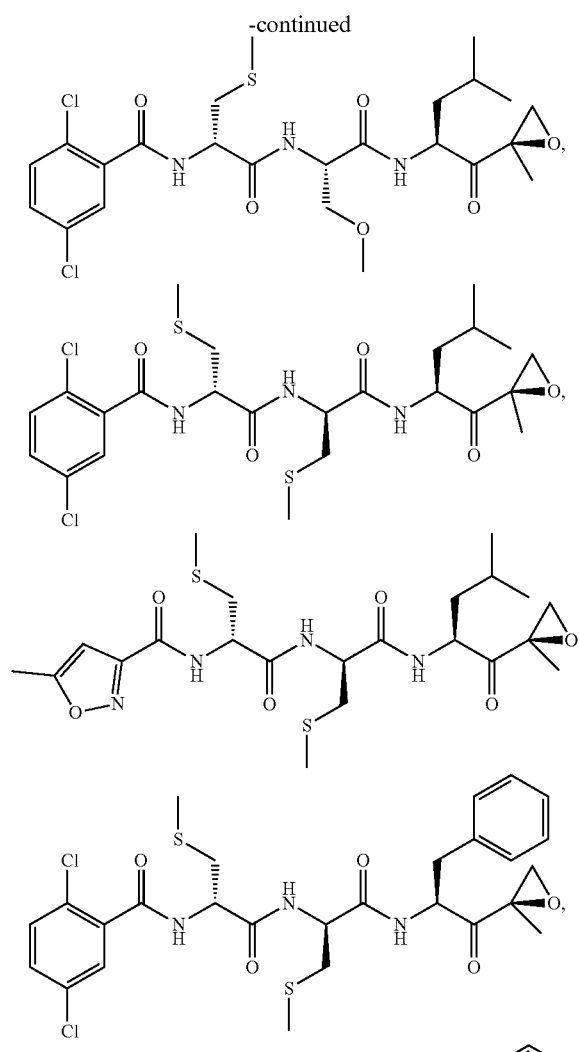
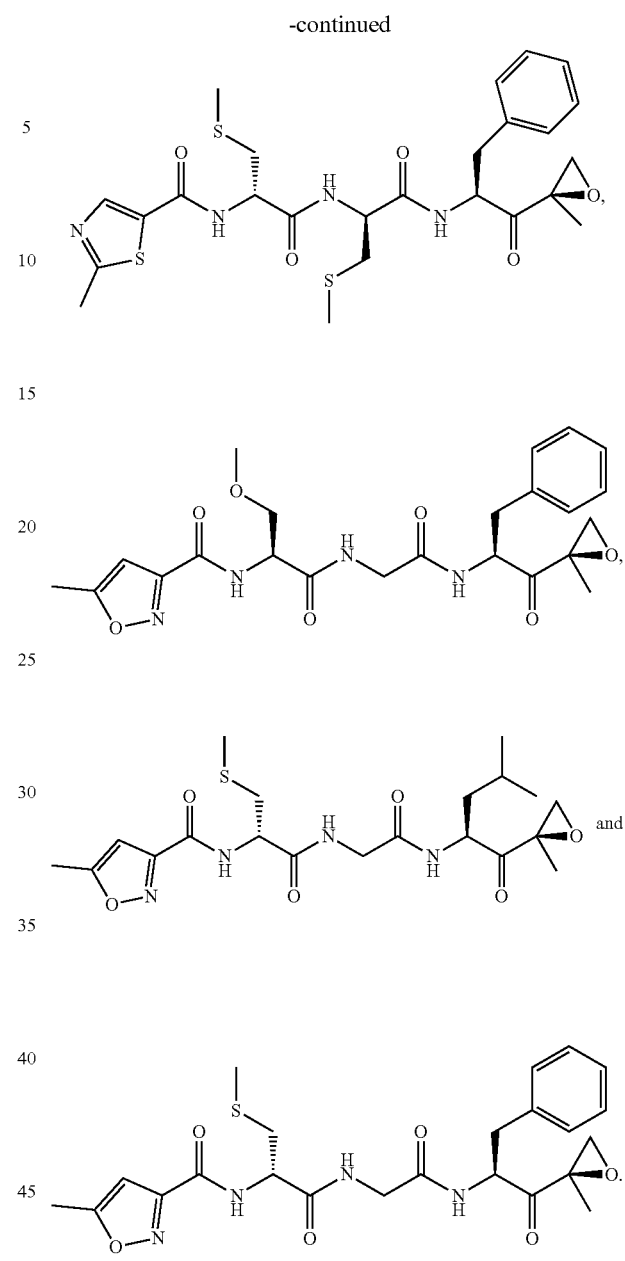

What is claimed is:
1. A tripeptide propylene oxide derivative or a pharmaceutically acceptable salt thereof, wherein
the tripeptide propylene oxide derivative is selected from the group consisting of

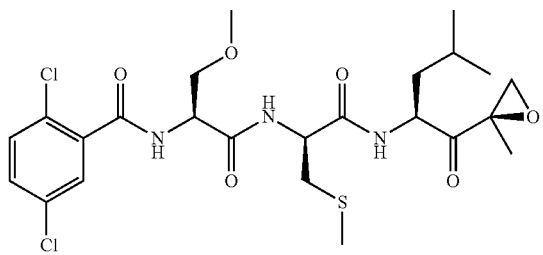

,

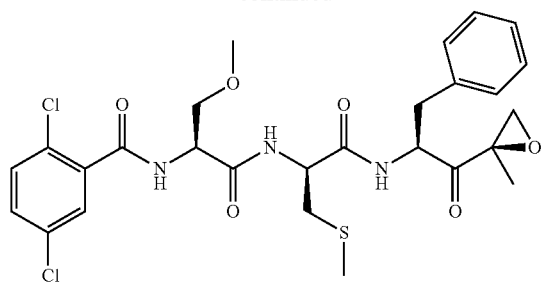

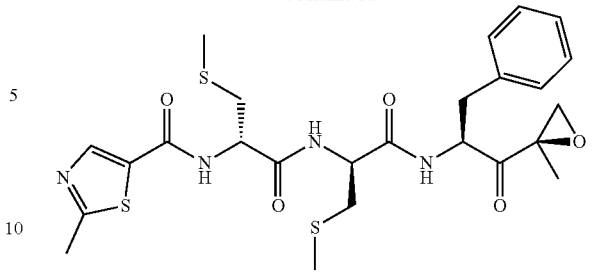

,

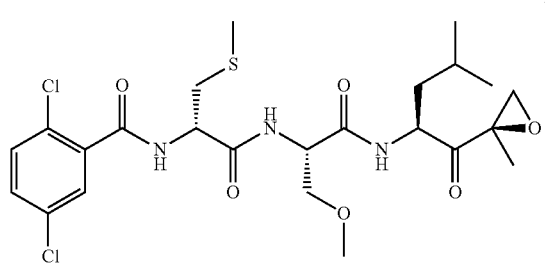

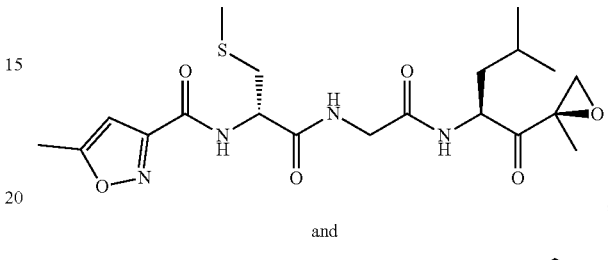

,

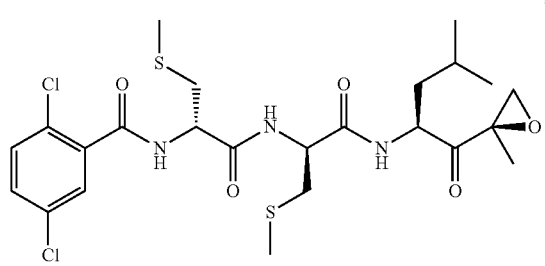

and

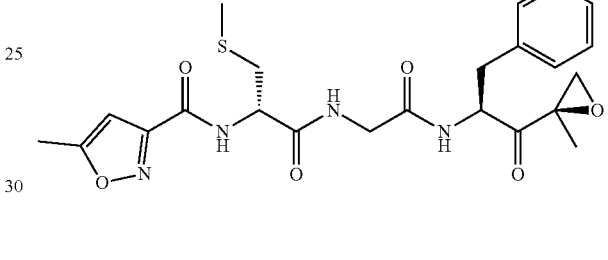

,

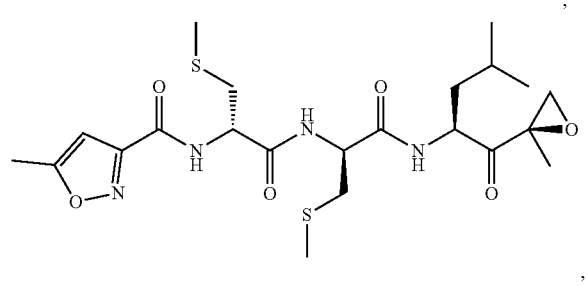

.

2. A pharmaceutical composition, comprising the tripeptide propylene oxide derivative or pharmaceutically acceptable salt thereof claim 1 and a pharmaceutically acceptable carrier.

3. A method for treating a myeloma comprising a step of administering an effective amount of a tripeptide propylene oxide derivative or pharmaceutically acceptable salt thereof to a subject in need thereof;

wherein
the tripeptide propylene oxide derivative is selected from the group consisting of

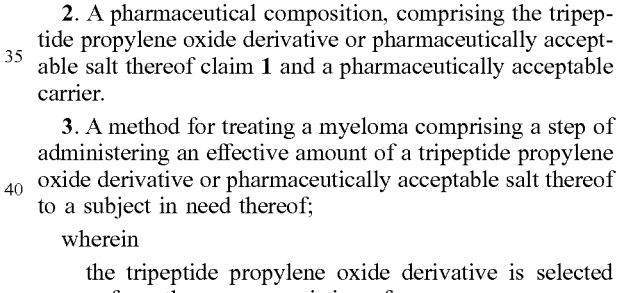

,

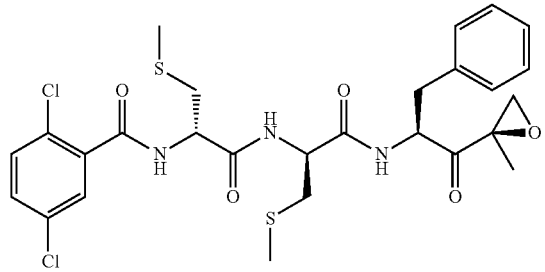

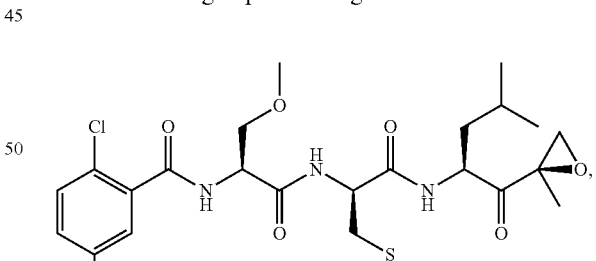

,

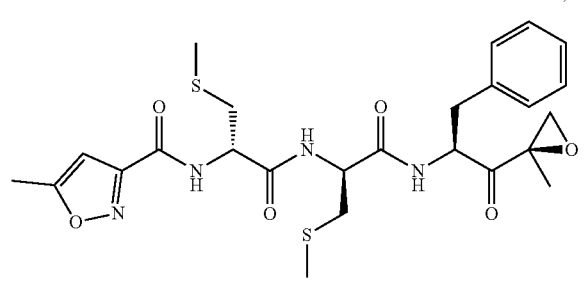

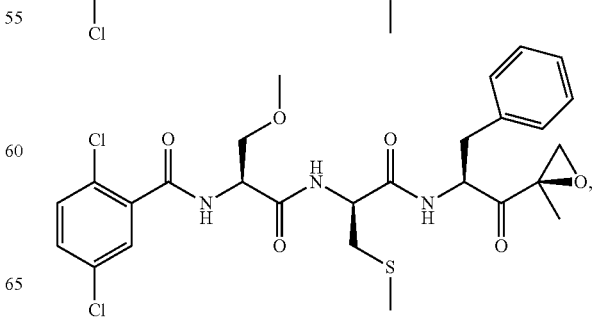

,